US012791370B2

(12) United States Patent
Winzer et al.

(10) Patent No.: US 12,791,370 B2
(45) Date of Patent: Nov. 10, 2026

(54) LASER DOPPLER VELOCIMETRY FLOW MEASUREMENT

(71) Applicant: Kardion GmbH, Stuttgart (DE)

(72) Inventors: Andreas Winzer, Ilmenau (DE); Christian Möller, Erfurt (DE); Johannes Stigloher, Stuttgart (DE)

(73) Assignee: Kardion GmbH, Stuttgart (DE)

( * ) Notice: Subject to any disclaimer, the term of this patent is extended or adjusted under 35 U.S.C. 154(b) by 414 days.

(21) Appl. No.: 18/349,399

(22) Filed: Jul. 10, 2023

(65) Prior Publication Data

US 2024/0011808 A1 Jan. 11, 2024

Related U.S. Application Data

(60) Provisional application No. 63/368,137, filed on Jul. 11, 2022.

(51) Int. Cl.

| | |
|---|---|
| ***A61M 60/523*** | (2021.01) |
| ***A61M 60/13*** | (2021.01) |
| ***A61M 60/216*** | (2021.01) |
| ***A61M 60/408*** | (2021.01) |

(Continued)

(52) U.S. Cl.

CPC ............ *G01F 1/663* (2013.01); *A61M 60/13* (2021.01); *A61M 60/216* (2021.01); *A61M 60/408* (2021.01); *G01F 1/661* (2013.01)

(58) Field of Classification Search

None

See application file for complete search history.

(56) References Cited

U.S. PATENT DOCUMENTS

| | | | |
|---|---|---|---|
| 3,088,323 | A | 5/1963 | Welkowitz et al. |
| 4,023,562 | A | 5/1977 | Hynecek et al. |
| 4,559,952 | A | 12/1985 | Angelsen et al. |

(Continued)

FOREIGN PATENT DOCUMENTS

| | | |
|---|---|---|
| CA | 3 122 415 | 7/2020 |
| CN | 1192351 A | 9/1998 |

(Continued)

OTHER PUBLICATIONS

Atkinson et al., "Pulse-Doppler Ultrasound and Its Clinical Application", The Yale Journal of Biology and Medicine, 1977, vol. 50, pp. 367-373.

(Continued)

*Primary Examiner* — Jon Eric C Morales

(74) *Attorney, Agent, or Firm* — Knobbe, Martens, Olson & Bear, LLP

(57) ABSTRACT

Systems, devices and method for laser Doppler-based fluid flow analysis. A Laser Doppler Velocimetry (LDV) technique may be used to analyze fluid flows in various contexts, such as blood flow in mechanical circulatory support (MCS) systems, and in other applications. Fluid velocity and volumetric flow may be measured. A laser source, optical fiber, and/or a photodiode may be used. Some embodiments may assess particulate parameters such as hemoglobin concentration in blood, reduce spectral noise via flow disturbance, reduce spectral noise using light of particular wavelength ranges, reduce noise via data analysis and signal processing techniques, and/or determine flow rate based on a non-linear relationship between a first weighted moment and the fluid flow.

21 Claims, 16 Drawing Sheets

(51) Int. Cl.
*G01F 1/661* (2022.01)
*G01F 1/663* (2022.01)

(56) References Cited

U.S. PATENT DOCUMENTS 4,680,730 A 7/1987 Omoda
4,781,525 A 11/1988 Hubbard et al.
4,888,011 A 12/1989 Kung et al.
4,889,131 A 12/1989 Salem et al.
5,045,051 A 9/1991 Milder et al.
5,269,811 A 12/1993 Hayes
5,289,821 A 3/1994 Swartz
5,581,038 A 12/1996 Lampropoulos
5,606,972 A 3/1997 Routh
5,662,115 A 9/1997 Torp
5,676,651 A 10/1997 Larson, Jr. et al.
5,695,471 A 12/1997 Wampler
5,720,771 A 2/1998 Snell
5,752,976 A 5/1998 Duffin et al.
5,827,203 A 10/1998 Nita
5,865,759 A 2/1999 Koblanski
5,888,242 A 3/1999 Antaki et al.
5,904,708 A 5/1999 Goedeke
5,911,685 A 6/1999 Siess et al.
5,964,694 A 10/1999 Siess et al.
5,980,465 A 11/1999 Elgas
6,007,478 A 12/1999 Siess et al.
6,024,704 A 2/2000 Meador et al.
6,053,873 A 4/2000 Govari et al.
6,167,765 B1 1/2001 Weitzel
6,176,822 B1 1/2001 Nix et al.
6,190,324 B1 2/2001 Kieval et al.
6,231,498 B1 5/2001 Pfeiffer et al.
6,245,007 B1 6/2001 Bedingham et al.
6,293,901 B1 9/2001 Prem
6,314,322 B1 11/2001 Rosenberg
6,351,048 B1 2/2002 Schob et al.
6,398,734 B1 6/2002 Cimochowski et al.
6,432,136 B1 8/2002 Weiss et al.
6,438,409 B1 8/2002 Malik et al.
6,512,949 B1 1/2003 Combs et al.
6,530,876 B1 3/2003 Spence
6,540,658 B1 4/2003 Fasciano et al.
6,540,659 B1 4/2003 Milbocker
6,561,975 B1 5/2003 Pool et al.
6,579,257 B1 6/2003 Elgas et al.
6,602,182 B1 8/2003 Milbocker
6,731,976 B2 5/2004 Penn et al.
6,879,126 B2 4/2005 Paden et al.
6,912,423 B2 6/2005 Ley et al.
6,949,066 B2 9/2005 Bearnson et al.
7,010,954 B2 3/2006 Siess
7,022,100 B1 4/2006 Aboul-Hosn et al.
7,024,244 B2 4/2006 Muhlenberg et al.
7,070,555 B2 7/2006 Siess
7,177,681 B2 2/2007 Xhu
7,513,864 B2 4/2009 Kantrowitz et al.
7,520,850 B2 4/2009 Brockway
7,526,338 B1 4/2009 Gill
7,527,599 B2 5/2009 Hickey
7,591,777 B2 9/2009 LaRose
7,744,560 B2 6/2010 Struble
7,856,335 B2 12/2010 Morello et al.
7,862,501 B2 1/2011 Woodward et al.
7,951,129 B2 5/2011 Chinchoy
7,963,905 B2 6/2011 Salmonsen et al.
7,988,728 B2 8/2011 Ayre
8,211,028 B2 7/2012 Karamanoglu et al.
8,435,182 B1 5/2013 Tamura
8,449,444 B2 5/2013 Poirier
8,545,380 B2 10/2013 Farnan et al.
8,591,393 B2 11/2013 Walters et al.
8,594,790 B2 11/2013 Kjellstrom et al.
8,622,949 B2 1/2014 Zafirelis et al.
8,657,875 B2 2/2014 Kung et al.
8,715,151 B2 5/2014 Poirier
8,747,293 B2 6/2014 Arndt et al.
8,849,398 B2 9/2014 Evans
8,864,644 B2 10/2014 Yomtov
8,876,685 B2 11/2014 Crosby et al.
8,882,477 B2 11/2014 Fritz, IV et al.
8,888,728 B2 11/2014 Aboul-Hosn et al.
8,897,873 B2 11/2014 Schima et al.
8,903,492 B2 12/2014 Soykan et al.
9,297,735 B2 3/2016 Graichen et al.
9,345,824 B2 5/2016 Mohl et al.
9,427,508 B2 8/2016 Reyes et al.
9,427,509 B2 8/2016 Vodermayer
9,474,840 B2 10/2016 Siess
9,492,601 B2 11/2016 Casas et al.
9,511,179 B2 12/2016 Casas et al.
9,555,173 B2 1/2017 Spanier
9,555,175 B2 1/2017 Bulent et al.
9,556,873 B2 1/2017 Yanai et al.
9,566,374 B2 2/2017 Spence et al.
9,636,442 B2 5/2017 Karmon et al.
9,656,010 B2 5/2017 Burke
9,669,142 B2 6/2017 Spanier et al.
9,669,144 B2 6/2017 Spanier et al.
9,713,701 B2 7/2017 Sarkar et al.
9,744,282 B2 8/2017 Rosenberg et al.
9,789,236 B2 10/2017 Bonde
9,833,550 B2 12/2017 Siess
9,848,899 B2 12/2017 Sliwa et al.
9,878,087 B2 1/2018 Richardson et al.
9,943,236 B2 4/2018 Bennett et al.
9,950,102 B2 4/2018 Spence et al.
9,999,714 B2 6/2018 Spanier et al.
10,010,662 B2 7/2018 Wiesener et al.
10,029,037 B2 7/2018 Muller et al.
10,052,420 B2 8/2018 Medvedev et al.
10,322,217 B2 6/2019 Spence
10,342,906 B2 7/2019 D'Ambrosio et al.
10,350,342 B2 7/2019 Thomas et al.
10,357,598 B2 7/2019 Aboul-Hosn et al.
10,376,162 B2 8/2019 Edelman et al.
10,413,651 B2 9/2019 Yomtov et al.
10,500,322 B2 12/2019 Karch
10,549,020 B2 2/2020 Spence et al.
10,561,771 B2 2/2020 Heilman et al.
10,561,772 B2 2/2020 Schumacher
10,561,773 B2 2/2020 Ferrari et al.
10,660,998 B2 5/2020 Hodges
10,668,195 B2 6/2020 Flores
10,864,308 B2 12/2020 Muller et al.
11,027,114 B2 6/2021 D'Ambrosio et al.
RE48,649 E 7/2021 Siess
11,147,960 B2 10/2021 Spanier et al.
11,273,299 B2 3/2022 Wolman et al.
11,285,310 B2 3/2022 Curran et al.
11,298,524 B2 4/2022 El Katerji et al.
11,320,382 B2 5/2022 Aikawa
11,324,395 B2 5/2022 Banik et al.
11,331,082 B2 5/2022 Itoh et al.
11,357,968 B2 6/2022 El Katerji et al.
11,389,639 B2 7/2022 Casas
11,478,629 B2 10/2022 Harjes et al.
11,524,165 B2 12/2022 Tan et al.
11,529,062 B2 12/2022 Moyer et al.
11,581,083 B2 2/2023 El Katerji et al.
11,622,695 B1 4/2023 Adriola et al.
11,628,293 B2 4/2023 Gandhi et al.
11,648,386 B2 5/2023 Poirer
11,653,841 B2 5/2023 Reyes et al.
11,666,746 B2 6/2023 Ferrari et al.
11,668,321 B2 6/2023 Richert et al.
11,684,276 B2 6/2023 Cros et al.
11,684,769 B2 6/2023 Harjes et al.
11,724,091 B2 8/2023 Siess et al.
11,779,234 B2 10/2023 Harjes et al.
11,781,551 B2 10/2023 Yanai et al.
11,790,487 B2 10/2023 Barbato et al.
11,793,994 B2 10/2023 Josephy et al.
11,806,116 B2 11/2023 Tuval et al.

(56) References Cited

U.S. PATENT DOCUMENTS 11,806,517 B2 11/2023 Petersen
11,813,079 B2 11/2023 Lau et al.
11,826,127 B2 11/2023 Casas
11,832,793 B2 12/2023 McWeeney et al.
11,832,868 B2 12/2023 Smail et al.
11,837,364 B2 12/2023 Lee et al.
11,844,592 B2 12/2023 Tuval et al.
11,844,940 B2 12/2023 D'Ambrosio et al.
11,850,073 B2 12/2023 Wright et al.
11,850,414 B2 12/2023 Schenck et al.
11,850,415 B2 12/2023 Schwammenthal et al.
11,857,345 B2 1/2024 Hanson et al.
11,864,878 B2 1/2024 Duval et al.
11,872,384 B2 1/2024 Cotter
11,883,207 B2 1/2024 El Katerji et al.
11,890,082 B2 2/2024 Cros et al.
11,896,199 B2 2/2024 Lent et al.
11,903,657 B2 2/2024 Geric et al.
11,906,411 B2 2/2024 Graichen et al.
11,911,550 B2 2/2024 Itamochi et al.
11,923,093 B2 3/2024 Moffitt et al.
11,931,073 B2 3/2024 Walsh et al.
11,931,528 B2 3/2024 Rohl et al.
11,986,274 B2 5/2024 Edelman
12,017,076 B2 6/2024 Tan et al.
12,023,476 B2 7/2024 Tuval et al.
12,029,891 B2 7/2024 Siess et al.
12,059,559 B2 8/2024 Muller et al.
12,076,544 B2 9/2024 Siess et al.
12,097,016 B2 9/2024 Goldvasser
12,102,815 B2 10/2024 Dhaliwal et al.
12,144,650 B2 11/2024 Spanier et al.
12,144,976 B2 11/2024 Baumbach et al.
12,178,554 B2 12/2024 Stotz et al.
12,179,009 B2 12/2024 El Katerji et al.
12,194,287 B2 1/2025 Kassel et al.
12,201,821 B2 1/2025 Schlebusch et al.
12,222,267 B2 2/2025 Stotz et al.
12,251,551 B2 3/2025 Liu et al.
12,257,424 B2 3/2025 Schlebusch et al.
12,268,861 B2 4/2025 D'Ambrosio et al.
12,296,158 B2 5/2025 Higgins et al.
12,310,621 B2 5/2025 Murphy
12,310,708 B2 5/2025 Schlebusch et al.
12,311,160 B2 5/2025 Schlebusch et al.
12,324,906 B2 6/2025 Baumbach et al.
12,329,501 B2 6/2025 Moyer et al.
12,329,956 B2 6/2025 Sunagawa
12,329,959 B2 6/2025 Hassan et al.
12,343,518 B2 7/2025 Tuval et al.
12,377,256 B2 8/2025 Stotz et al.
12,390,168 B2 8/2025 Katerji et al.
12,409,311 B2 9/2025 Jahangir et al.
12,409,313 B2 9/2025 Eggen et al.
12,424,315 B2 9/2025 Nix et al.
12,434,060 B2 10/2025 Tan et al.
12,440,665 B2 10/2025 Tuval et al.
12,451,230 B2 10/2025 El Katerji et al.
12,478,266 B2 11/2025 Edelman et al.
12,478,267 B2 11/2025 Schlebusch et al.
12,478,774 B2 11/2025 Muller
12,491,357 B2 12/2025 Baumbach et al.
12,494,292 B2 12/2025 El Katerji et al.
12,502,524 B2 12/2025 Stigloher et al.
12,508,418 B2 12/2025 Baumbach et al.
12,544,556 B2 2/2026 Tuval et al.
12,569,671 B2 3/2026 Schellenberg et al.
12,575,841 B2 3/2026 Gao et al.
12,576,261 B2 3/2026 Vasudevan Jalaja et al.
12,589,239 B2 3/2026 Gandhi et al.
12,611,535 B2 4/2026 Segura Ortega et al.
12,629,508 B2 5/2026 Tuval et al.
2001/0016686 A1 8/2001 Okada et al.
2001/0039828 A1 11/2001 Shin et al.
2002/0022785 A1 2/2002 Romano
2002/0082585 A1 6/2002 Carroll et al.
2002/0093412 A1 7/2002 Morrison
2002/0147495 A1 10/2002 Petroff
2002/0151761 A1 10/2002 Viole et al.
2003/0130581 A1 7/2003 Salo et al.
2003/0139643 A1 7/2003 Smith et al.
2003/0167002 A1 9/2003 Nagar et al.
2003/0191357 A1 10/2003 Frazier
2003/0199727 A1 10/2003 Burke
2004/0022640 A1 2/2004 Siess et al.
2004/0044266 A1 3/2004 Siess et al.
2004/0065143 A1 4/2004 Husher
2004/0124979 A1 7/2004 Medema
2004/0130009 A1 7/2004 Tangpuz
2004/0167376 A1 8/2004 Peters et al.
2004/0167410 A1 8/2004 Hettrick
2004/0225177 A1 11/2004 Coleman et al.
2004/0241019 A1 12/2004 Goldowsky
2004/0260346 A1 12/2004 Overall et al.
2005/0001324 A1 1/2005 Dunn
2005/0046044 A1 3/2005 Theuss
2005/0126268 A1 6/2005 Ouriev et al.
2005/0187487 A1 8/2005 Azizkhan
2006/0108697 A1 5/2006 Wang
2006/0108901 A1 5/2006 Mao-Chin et al.
2006/0122583 A1 6/2006 Pesach et al.
2006/0196277 A1 9/2006 Allen et al.
2006/0229488 A1 10/2006 Ayre et al.
2006/0287600 A1 12/2006 McEowen
2006/0287604 A1 12/2006 Hickey
2007/0060787 A1 3/2007 Peters et al.
2007/0069354 A1 3/2007 Dangelmaier
2007/0073352 A1 3/2007 Euler et al.
2007/0088214 A1 4/2007 Shuros et al.
2007/0156006 A1 7/2007 Smith et al.
2007/0255352 A1 11/2007 Roline et al.
2007/0266778 A1 11/2007 Corey et al.
2007/0282209 A1 12/2007 Lui et al.
2007/0299325 A1 12/2007 Farrell et al.
2008/0015517 A1 1/2008 Geistert et al.
2008/0082005 A1 4/2008 Stern et al.
2008/0091239 A1 4/2008 Johansson et al.
2008/0097595 A1 4/2008 Gabbay
2008/0102096 A1 5/2008 Molin et al.
2008/0108901 A1 5/2008 Baba et al.
2008/0108930 A1 5/2008 Weitzel et al.
2008/0133006 A1 6/2008 Crosby et al.
2008/0146996 A1 6/2008 Smisson
2008/0210016 A1 9/2008 Zwirn et al.
2008/0248614 A1 10/2008 Yang
2008/0262289 A1 10/2008 Goldowsky
2008/0262361 A1 10/2008 Gutfinger et al.
2008/0269822 A1 10/2008 Ljungstrom et al.
2008/0275339 A1 11/2008 Thiemann et al.
2008/0287799 A1 11/2008 Hall
2008/0306328 A1 12/2008 Ercolani
2009/0024042 A1 1/2009 Nunez et al.
2009/0025459 A1 1/2009 Zhang et al.
2009/0064755 A1 3/2009 Fleischli et al.
2009/0105799 A1 4/2009 Hekmat et al.
2009/0131765 A1 5/2009 Roschak et al.
2009/0204163 A1 8/2009 Shuros et al.
2009/0212637 A1 8/2009 Baarman et al.
2009/0312650 A1 12/2009 Maile et al.
2010/0010354 A1 1/2010 Skerl et al.
2010/0082099 A1 4/2010 Vodermayer et al.
2010/0160801 A1 6/2010 Takatani et al.
2010/0191035 A1 7/2010 Kang et al.
2010/0268017 A1 10/2010 Siess
2010/0298625 A1 11/2010 Reichenbach et al.
2010/0324378 A1 12/2010 Tran et al.
2011/0004075 A1 1/2011 Stahmann et al.
2011/0022057 A1 1/2011 Eigler et al.
2011/0144744 A1 6/2011 Wampler
2011/0160516 A1 6/2011 Dague
2011/0172505 A1 7/2011 Kim
2011/0184301 A1 7/2011 Holmstrom
2011/0186943 A1 8/2011 Pahl
2011/0218435 A1 9/2011 Srinivasan et al.

(56) References Cited

U.S. PATENT DOCUMENTS

2011/0230068 A1 9/2011 Pahl
2012/0029408 A1 2/2012 Beaudin
2012/0084024 A1 4/2012 Norcross, Jr.
2012/0150089 A1 6/2012 Penka et al.
2012/0150291 A1 6/2012 Aber
2012/0197141 A1 8/2012 Vanney
2012/0203476 A1 8/2012 Dam
2012/0245404 A1 9/2012 Smith
2012/0247200 A1 10/2012 Ahonen et al.
2012/0310037 A1 12/2012 Choi et al.
2012/0330214 A1 12/2012 Peters et al.
2013/0041204 A1 2/2013 Heilman et al.
2013/0066142 A1 3/2013 Doerr et al.
2013/0072846 A1 3/2013 Heide et al.
2013/0116575 A1 5/2013 Mickle et al.
2013/0144379 A1 6/2013 Najafi et al.
2013/0280692 A1 10/2013 Gourlay
2013/0289376 A1 10/2013 Lang
2013/0303831 A1 11/2013 Evans
2013/0304404 A1 11/2013 Dam
2014/0013852 A1 1/2014 Brown et al.
2014/0030122 A1 1/2014 Ozaki
2014/0100414 A1 4/2014 Tamez et al.
2014/0114202 A1 4/2014 Hein et al.
2014/0200389 A1 7/2014 Yanai et al.
2014/0243688 A1 8/2014 Caron et al.
2014/0275720 A1 9/2014 Ferrari
2014/0275727 A1 9/2014 Bonde
2014/0296677 A1 10/2014 McEowen
2014/0303426 A1 10/2014 Kerkhoffs et al.
2014/0342203 A1 11/2014 Elian
2015/0027224 A1 1/2015 Schiffer
2015/0080743 A1 3/2015 Siess
2015/0141832 A1 5/2015 Yu et al.
2015/0141842 A1 5/2015 Spanier et al.
2015/0157216 A1 6/2015 Stigall et al.
2015/0174307 A1 6/2015 Eckman et al.
2015/0190092 A1 7/2015 Mori
2015/0196076 A1 7/2015 Billingslea
2015/0200562 A1 7/2015 Kilinc et al.
2015/0201900 A1 7/2015 Syed
2015/0250935 A1 9/2015 Anderson et al.
2015/0273184 A1 10/2015 Scott et al.
2015/0290372 A1 10/2015 Muller et al.
2015/0306290 A1 10/2015 Rosenberg et al.
2015/0306291 A1 10/2015 Bonde et al.
2015/0307344 A1 10/2015 Ernst
2015/0327921 A1 11/2015 Govari
2015/0335804 A1 11/2015 Marseille et al.
2015/0365738 A1 12/2015 Purvis et al.
2016/0000983 A1 1/2016 Mohl et al.
2016/0008531 A1 1/2016 Wang et al.
2016/0022890 A1 1/2016 Schwammenthal et al.
2016/0045165 A1 2/2016 Braido et al.
2016/0144166 A1 5/2016 Decréet al.
2016/0151553 A1 6/2016 Bonde
2016/0166747 A1 6/2016 Frazier et al.
2016/0213828 A1 7/2016 Sievers
2016/0278856 A1 9/2016 Panescu
2016/0302672 A1 10/2016 Kuri
2016/0303299 A1 10/2016 Muller
2016/0317043 A1 11/2016 Campo
2016/0338629 A1 11/2016 Doerr
2017/0010144 A1 1/2017 Lenner et al.
2017/0021070 A1 1/2017 Petersen
2017/0049945 A1 2/2017 Halvorsen et al.
2017/0086780 A1 3/2017 Sokulin et al.
2017/0098491 A1 4/2017 Ziaie et al.
2017/0128646 A1 5/2017 Karch
2017/0202575 A1 7/2017 Stanfield et al.
2017/0224279 A1 8/2017 Cahan et al.
2017/0239407 A1 8/2017 Hayward
2017/0258980 A1 9/2017 Katsuki et al.
2017/0258981 A1 9/2017 Franano
2017/0340789 A1 11/2017 Bonde et al.
2017/0348470 A1 12/2017 D'Ambrosio et al.
2017/0354812 A1 12/2017 Callaghan et al.
2018/0021497 A1 1/2018 Nunez
2018/0064860 A1 3/2018 Nunez et al.
2018/0078159 A1 3/2018 Edelman et al.
2018/0093070 A1 4/2018 Cottone
2018/0110910 A1 4/2018 Rodemerk et al.
2018/0126053 A1 5/2018 Zilbershlag et al.
2018/0199635 A1 7/2018 Longinotti-Buitoni et al.
2018/0264182 A1 9/2018 Spanier et al.
2018/0280598 A1 10/2018 Curran et al.
2018/0326131 A1 11/2018 Muller et al.
2018/0333059 A1 11/2018 Casas
2018/0353667 A1 12/2018 Moyer et al.
2019/0054223 A1 2/2019 Frazier et al.
2019/0083690 A1 3/2019 Siess et al.
2019/0217002 A1 7/2019 Urakabe
2019/0240680 A1 8/2019 Hayakawa
2019/0254543 A1 8/2019 Hartholt et al.
2019/0282741 A1 9/2019 Franano et al.
2019/0282744 A1 9/2019 D'Ambrosio et al.
2019/0351117 A1 11/2019 Cambronne et al.
2019/0351118 A1 11/2019 Graichen et al.
2020/0016309 A1 1/2020 Kallenbach et al.
2020/0028376 A1 1/2020 Ha
2020/0038567 A1 2/2020 Siess et al.
2020/0147283 A1 5/2020 Tanner et al.
2020/0164125 A1 5/2020 Muller et al.
2020/0164126 A1 5/2020 Muller
2020/0253583 A1 8/2020 Brisken et al.
2021/0268264 A1 9/2021 Stotz
2021/0290087 A1 9/2021 Schlebusch
2021/0290930 A1 9/2021 Kasel
2021/0290933 A1 9/2021 Stotz
2021/0339002 A1 11/2021 Schlebusch et al.
2021/0339004 A1 11/2021 Schlebusch et al.
2021/0346674 A1 11/2021 Baumbach et al.
2021/0346675 A1 11/2021 Schlebusch et al.
2021/0346676 A1 11/2021 Schlebusch et al.
2021/0346677 A1 11/2021 Baumbach et al.
2021/0346678 A1 11/2021 Baumbach et al.
2021/0378523 A1 12/2021 Budde
2021/0379359 A1 12/2021 Schellenberg
2021/0379360 A1 12/2021 Schellenberg
2022/0016411 A1 1/2022 Winterwerber
2022/0032032 A1 2/2022 Schlebusch et al.
2022/0032036 A1 2/2022 Baumbach et al.
2022/0039669 A1 2/2022 Schlebusch et al.
2022/0047173 A1 2/2022 Stotz et al.
2022/0050037 A1 2/2022 Stotz et al.
2022/0072298 A1 3/2022 Spanier et al.
2022/0079457 A1 3/2022 Tuval et al.
2022/0105339 A1 4/2022 Nix et al.
2022/0126086 A1 4/2022 Schlebusch et al.
2022/0142462 A1 5/2022 Douk et al.
2022/0161019 A1 5/2022 Mitze et al.
2022/0361762 A1 11/2022 Lalancette
2023/0173250 A1* 6/2023 Stigloher .............. G01S 13/505 600/17
2023/0191141 A1 6/2023 Wenning et al.
2024/0245902 A1 7/2024 Schlebusch et al.
2025/0032773 A1 1/2025 Baumbach et al.
2025/0121177 A1 4/2025 West
2025/0143587 A1 5/2025 Stotz
2025/0144397 A1 5/2025 Kassel et al.
2025/0222247 A1 7/2025 Schlebusch
2025/0235687 A1 7/2025 Schlebusch et al.
2025/0251330 A1 8/2025 Stotz
2025/0281060 A1 9/2025 Schlebusch et al.
2025/0319299 A1 10/2025 Stotz et al.
2025/0345590 A1 11/2025 Schlebusch et al.
2025/0367429 A1 12/2025 Eggen et al.
2025/0367431 A1 12/2025 Baumbach et al.
2026/0060557 A1 3/2026 Schlebusch et al.

(56) References Cited

U.S. PATENT DOCUMENTS

| | | | |
|---|---|---|---|
| 2026/0083959 | A1 | 3/2026 | Baumbach et al. |
| 2026/0115450 | A1 | 4/2026 | Stigloher et al. |

FOREIGN PATENT DOCUMENTS

| | | |
|---|---|---|
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 101711683 | 5/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 107530479 | 1/2018 |
| CN | 107632167 | 1/2018 |
| CN | 215841206 | 2/2022 |
| CN | 217828630 | 11/2022 |
| CN | 219250364 | 6/2023 |
| CN | 118320294 | 7/2024 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 20 2015 009 422 | 7/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 764 448 | 3/1997 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 2 143 385 | 1/2010 |
| EP | 2 175 770 | 4/2010 |
| EP | 2 570 143 | 3/2013 |
| EP | 2 859 911 | 4/2015 |
| EP | 2 213 227 | 8/2016 |
| EP | 3 088 016 | 11/2016 |
| EP | 2 945 661 | 11/2017 |
| EP | 2 136 861 | 12/2017 |
| EP | 3 287 154 | 2/2018 |
| EP | 3 205 359 | 8/2018 |
| EP | 3 205 360 | 8/2018 |
| EP | 3 378 421 | 9/2018 |
| EP | 2 505 090 | 12/2019 |
| EP | 3 668 560 | 6/2020 |
| EP | 3 753 594 | 12/2020 |
| EP | 3 487 548 | 3/2021 |
| EP | 3 615 103 | 3/2021 |
| EP | 3 131 615 | 6/2021 |
| EP | 3 463 505 | 9/2021 |
| EP | 3 884 970 | 9/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 689 389 | 3/2022 |
| EP | 3 737 436 | 3/2022 |
| EP | 3 972 661 | 3/2022 |
| EP | 3 984 589 | 4/2022 |
| EP | 3 654 006 | 5/2022 |
| EP | 2 999 400 | 8/2022 |
| EP | 3 600 477 | 10/2022 |
| EP | 3 897 768 | 10/2022 |
| EP | 2 892 583 | 1/2023 |
| EP | 3 597 231 | 1/2023 |
| EP | 3 003 420 | 2/2023 |
| EP | 3 046 594 | 3/2023 |
| EP | 3 938 005 | 4/2023 |
| EP | 3 809 959 | 7/2023 |
| EP | 2 072 150 | 9/2023 |
| EP | 3 768 156 | 9/2023 |
| EP | 4 052 754 | 10/2023 |
| EP | 4 252 825 | 10/2023 |
| EP | 4 252 826 | 10/2023 |
| EP | 4 252 828 | 10/2023 |
| EP | 3 157 596 | 11/2023 |
| EP | 3 766 428 | 11/2023 |
| EP | 3 781 027 | 11/2023 |
| EP | 4 070 720 | 11/2023 |
| EP | 3 687 596 | 12/2023 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 397 147 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 3 809 960 | 12/2024 |
| EP | 4 477 250 | 12/2024 |
| EP | 4 483 940 | 1/2025 |
| EP | 4 491 213 | 1/2025 |
| EP | 4 429 754 | 2/2025 |
| EP | 3 970 785 | 3/2025 |
| EP | 4 429 753 | 3/2025 |
| EP | 3 950 043 | 5/2025 |
| EP | 4 039 319 | 6/2025 |
| EP | 3 668 559 | 8/2025 |
| EP | 3 848 088 | 8/2025 |
| EP | 4 218 556 | 9/2025 |
| EP | 3 548 109 | 1/2026 |
| EP | 4 099 898 | 1/2026 |
| EP | 3 579 893 | 2/2026 |
| EP | 4 090 412 | 4/2026 |
| EP | 3 852 833 | 5/2026 |
| EP | 4 188 511 | 5/2026 |
| EP | 4 223 356 | 5/2026 |
| EP | 4 252 827 | 5/2026 |
| ES | 2 913 485 | 6/2022 |
| GB | 2 504 177 | 1/2014 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |

(56) References Cited

FOREIGN PATENT DOCUMENTS

| | | |
|---|---|---|
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-503495 | 2/2010 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-508128 | 3/2019 |
| JP | 2019-523110 | 8/2019 |
| JP | 2019-509141 | 2/2022 |
| WO | WO 89/006513 | 1/1989 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/147291 | 8/2017 |
| WO | WO 2017/214118 | 12/2017 |
| WO | WO 2018/005228 | 1/2018 |
| WO | WO 2018/048800 | 3/2018 |
| WO | WO 2018/213089 | 11/2018 |
| WO | WO 2019/034670 | 2/2019 |
| WO | WO 2019/078723 | 4/2019 |
| WO | WO 2019/126721 | 6/2019 |
| WO | WO 2019/158996 | 8/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/243756 | 12/2020 |
| WO | WO 2021/159001 | 8/2021 |
| WO | WO 2023/040546 | 12/2021 |
| WO | WO 2022/074136 | 4/2022 |
| WO | WO 2022/109590 | 5/2022 |
| WO | WO 2022/173970 | 8/2022 |
| WO | WO 2023/226779 | 9/2022 |
| WO | WO 2023/037162 | 3/2023 |
| WO | WO 2023/049813 | 3/2023 |
| WO | WO 2023/230157 | 11/2023 |
| WO | WO 2024/104184 | 5/2024 |
| WO | WO 2026/072583 | 4/2026 |

OTHER PUBLICATIONS

Hertz Ph.D. et al, "Ultrasonic Engineering in Heart Diagnosis", The American Journal of Cardiology, Jan. 1967, vol. 19, No. 1, pp. 6-17.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

Leguy et al., "Assessment of Blood Volume Flow in Slightly Curved Arteries from a Single Velocity Profile", Journal of Biomechanics, 2009, pp. 1664-1672.

Lombardi et al., "Flow Rate Profiler: an instrument to measure blood velocity profiles", Ultrasonics, 2001, vol. 39, pp. 143-150.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Sinha et al., "Effect of Mechanical Assistance of the Systemic Ventricle in Single Ventricle Circulation with Cavopulmonary Connection", The Journal of Throacic and Cardiovascular Surgery, Apr. 2014, vol. 147, No. 4, pp. 1271-1275.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

"Understanding Hot-Wire Anemometry", Advanced Thermal Solutions, Inc., 2007, pp. 13-17.

Vieli, A., "Doppler Flow Determination", BJA: British Journal of Anaesthesia, 1988, vol. 60, pp. 107S-112S.

Yuanyuan et al., "Characteristics Analysis for Doppler Ultrasound Blood Flow Signals", China Medical Device Information, 5(1), Feb. 28, 1999, pp. 36-42.

(56) References Cited

OTHER PUBLICATIONS

Zhang, Dabiao et al., "Design of Microwave Velocity and Distance Monitor System", Instrument Technique and Sensor, Hebei Normal University, Apr. 25, 2004, pp. 3.
Chung et al., "Improved Efficiency Characteristics of Wireless Power Charging System for Superconducting MAGLEV Train Using Inserted Permanent Magnets," 2018 IEEE International Symposium on Electromagnetic Compatibility, 2018, pp. 564-567.
"ECG Electrodes product comparison chart," 3M.com, 2018, https://multimedia.3m.com/mws/media/1490883O/red-dot-ecg-electrodes-comparison-chart.pdf, accessed May 18, 2025, 1 page.
Eeckhout, MD, Phd, et al., "Handbook of Complications During Percutaneous Cardiovascular Interventions", 2007 Informa UK Ltd., Ch. 12, pp. 167-177.
Mack-Haynes, Robin, "Fasteners Made Easy," New Mexico State University, https://pubs.nmsu.edu/_c/C232.pdf, accessed May 18, 2025, pp. 8.
Mullins, Charles E., Md, "Cardiac Catheterization in Congenital Heart Disease: Pediatric and Adult", Blackwell Futura, 2006, Chapters 3, 4 and 32, pp. 101.
Radiologyinfo.org, "Subcutaneous Port," Definition, https://www.radiologyinfo.org/en/glossary?id=ezNFREEzNEFFLTI5OTAtNDVFNy04MkVBLTA1RDVGMDdBMzNFRH0=&i=1&b=0&modal=1, accessed Sep. 2, 2025, 1 page.
Tan et al., "Surface Engineering and Patterning Using Parylene for Biological Applications." Materials, Mar. 15, 2010, vol. 3, No. 3, pp. 1803-1832.
Walser, Eric, "Venous access ports: indications, implantation technique, follow-up, and complications;" Cardiovasc Intervent Radial, Aug. 2012; vol. 35, No. 4, pp. 751-764. (Abstract Only).

* cited by examiner

LASER DOPPLER VELOCIMETRY FLOW MEASUREMENT

INCORPORATION BY REFERENCE TO RELATED APPLICATIONS

Any and all applications for which a foreign or domestic priority claim is identified in the Application Data Sheet as filed with the present application are hereby incorporated by reference under 37 CFR 1.57. For example, this application claims priority to U.S. Provisional Patent Application 63/368,137, entitled "LASER DOPPLER VELOCIMETRY FLOW MEASUREMENT" Filed Jul. 11, 2022, the entire content of which is incorporated by reference herein in its entirety for all purposes and forms a part of this specification.

BACKGROUND

Technical Field

The present disclosure is directed generally to fluid flow measurement, in particular to laser doppler velocimetry flow measurement, for example, in mechanical circulatory support systems to assess volumetric blood flow and other applications.

Description of the Related Art

Fluid flow measurement is useful in many contexts. For instance, measurement of blood flow in mechanical circulatory support (MCS) systems that assist with facilitating blood flow to increase cardiac output. Conventional approaches to measuring blood flow analyze operating parameters of the support system, such as electrical power consumed by a motor. However, such methods lack precision and are complex. There is therefore a need for improvements to these and other drawbacks to existing solutions to fluid flow measurement.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for fluid flow measurements.

The following disclosure describes non-limiting examples of some embodiments of laser doppler-based fluid flow measurement systems, devices, and methods. Other embodiments of the disclosed systems and methods may or may not include the features described herein. Moreover, disclosed advantages and benefits may apply only to certain embodiments and should not be used to limit the disclosure.

Various systems, devices and methods are described for laser Doppler-based fluid flow analysis. A Laser Doppler Velocimetry (LDV) technique may be used to analyze fluid flows in various contexts, such as blood flow in MCS systems, and in other applications. Fluid velocity and volumetric flow may be measured. A laser source, optical fiber, and/or a photodiode may be used. Some embodiments may assess particulate parameters such as hemoglobin concentration in blood, reduce spectral noise via flow disturbance, reduce spectral noise using light of particular wavelength ranges, reduce noise via data analysis and signal processing techniques, and/or determine flow rate based on a non-linear relationship between a first weighted moment and the fluid flow.

One example embodiment of laser Doppler-based fluid flow analysis includes fluid flow measurement in a mechanical circulatory support (MCS) system. However, while various aspects are described within the context of mechanical circulatory support (MCS) systems, the technology can be used in other applications as well. Various aspects may use components for conducting Laser Doppler Velocimetry (LDV) to measure volumetric flow of fluid in various contexts, for example, the flow of blood through an MCS system or through an aortic valve around an implanted MCS device.

In one aspect, a system for controlling a mechanical circulatory support (MCS) device and determining flow rate through the MCS device is described. The system may include a computerized MCS control console located at least in part outside a body of a patient. The computerized MCS control console may be in communication with the MCS device. The MCS device may be configured to be implanted in a body of a patient. A Laser Doppler Velocimetry (LDV) module may be in communication with the computerized MCS control console. The LDV module may be configured to measure a volumetric flow rate of blood of the patient. The LDV module may include a laser source, a photodiode, and one or more hardware processors.

Various embodiments of the various aspects may be implemented. In some embodiments, the MCS device may include an optical fiber extending from a proximal ex vivo region to a distal in vivo region. A distal terminating tip of the optical fiber may be positioned in an inlet cannula of the MCS device.

In one aspect, the MCS device may be configured to at least partially be implanted in a heart of a patient. The MCS device may include an inlet portion, an outflow portion, a catheter, a proximal hub, a connector and an optical fiber. The connector may be configured to connect the catheter to a control console. The optical fiber may extend from a proximal ex vivo region to a distal in vivo region. A distal terminating tip of the optical fiber may be positioned in the inlet portion of the mechanical circulatory support (MCS) device.

In some embodiments, the inlet portion may include an inlet cannula. In some embodiments, the MCS device may further include a micro-optic lens connected to the distal terminating tip. In some embodiments, at least a portion of the optical fiber may be positioned between a structural layer and a membrane of the inlet portion. In some embodiments, the MCS device may further include a second optical fiber. In some embodiments, the second optical fiber may have a measurement head or distal terminating tip positioned exterior to the MCS device. In some embodiments, at least a portion of the optical fiber may be positioned on an exterior surface of a structural layer of the inlet portion in a helical configuration. In some embodiments, the helical configuration may be aligned with a helical configuration of laser cuts in the structural layer.

In some embodiments, the MCS device may include a nose piece. In some embodiments, the distal terminating tip of the optical fiber may be positioned at least in part within the nose piece.

In another aspect, the MCS device may include a laser source, a photodiode, and a preamplifier. Various embodiments of the various aspects may be implemented. In some embodiments, the laser source and photodiode may be positioned in a nose piece of the MCS device. In some embodiments, the laser source may be a vertical-cavity surface-emitting laser. In some embodiments, the MCS device may further include an electrical conductor positioned on the exterior surface of a structural layer of an inlet cannula of the MCS device. In some embodiments, the electrical conductor may be positioned in a helical pattern around the inlet cannula of the MCS device.

In another aspect, a system for measuring hemoglobin concentration of a patient's blood with a MCS device is also described. The system may include a light source, a photodiode and one or more hardware processors. The light source may be configured to transmit light into the blood of a patient through an optical fiber coupled to the MCS device. The photodiode may be configured to capture light attenuated by the blood of the patient. The one or more hardware processors may be configured to receive the captured light from the photodiode. The one or more hardware processors may also be configured to calculate a measured light absorption based on an intensity of the captured light. The one or more hardware processors may also be configured to compare the measured light absorption to a hemoglobin model to determine a hemoglobin concentration. The hemoglobin model may include a relationship between light intensity and hemoglobin concentration. In some embodiments, the one or more hardware processors may also be configured to access values in a lookup table storing a relationship between light intensity and hemoglobin concentration to compare the light absorption to a hemoglobin model. In some embodiments, the one or more hardware processors may also be configured to compare the measured light absorption to values in the lookup table. In some embodiments, the light source may be configured to deliver a range of light frequencies. In some embodiments, the light source may be configured to deliver a range of light wavelengths.

In another aspect, a system for determining volumetric flowrate of blood through a tube geometry using Laser Doppler Velocimetry (LDV) is also described. The system may include a photodiode and one or more hardware processors. The photodiode may be configured to generate a signal associated with light attenuated by blood of a patient. The one or more hardware processors may be in communication with the photodiode and configured to execute a computer operable algorithm for reducing spectral noise in the signal.

In some embodiments, the system may further include an optical fiber configured to transmit light to, or receive light from, moving blood particles. In some embodiments, a distal end of the optical fiber may create a first flow disturbance in the moving blood. In some embodiments, a distal end of the optical fiber may also create at least one flow disturbance element for superimposing a second flow disturbance onto the first flow disturbance.

In some embodiments, the at least one flow disturbance element may be stationary with respect to the distal end of the optical fiber. In some embodiments, the at least one flow disturbance element may be upstream of the distal end of the optical fiber in a range of 0 to 20 cm, optionally in a range of 5 mm to 30 mm. In some embodiments, the at least one flow disturbance element may include a protrusion into the inner lumen of an inlet cannula. In some embodiments, the protrusion may have a width or diameter in a range of 0.2 mm to 1 mm.

In some embodiments, the at least one flow disturbance element may have a height long enough that the flow disturbance reaches the distal end of the optical fiber. In some embodiments, the height may be in a range of 0.1 mm to 1 mm.

In some embodiments, the at least one flow disturbance element may be a groove. In some embodiments, the groove may have a depth in a range of 0.5 to 1 mm. In some embodiments, the groove may have an angle to a direction of flow in a range of 15 to 90 degrees. In some embodiments, the at least one flow disturbance element may be a ridge. In some embodiments, the ridge may have a height in a range of 0.5 to 1 mm. In some embodiments, the ridge may have an angle to a direction of flow in a range of 15 to 90 degrees.

In some embodiments, the light may have a wavelength in a range of 390 nm to 750 nm. In some embodiments, the light may be configured to penetrate through blood deeper than 0.6 mm. In some embodiments, the light may have a wavelength in a range of 640 nm to 750 nm.

In another aspect, a system including an MCS device is described. The MCS device may include an electronic storage medium. The electronic storage medium may be configured to store a background frequency spectrum, $s_{bg}(f)$. The electronic storage medium may also be configured to store a relationship of velocity or flowrate with a first weighted moment of data spectra, v(fm).

In some embodiments, the background frequency spectrum $s_{bg}(f)$ may be based on an empirical measurement of light delivered to the MCS device in a test scenario. In some embodiments, the test scenario may include a scenario where the MCS test device is in contact with a fluid medium. In some embodiments, the fluid medium may include at least one of: still blood, a sterile medium having similar particles and scattering pattern to blood, and air. In some embodiments, the test scenario may be conducted using the MCS device or a sample of one or more MCS devices from a manufacturing batch of MCS devices.

In some embodiments, the one or more hardware processors may be configured to execute a flowrate determination algorithm. In some embodiments, the flowrate determination algorithm may include calculating a frequency spectrum s(f) from a measured photodiode signal. In some embodiments, the flowrate determination algorithm may include calculating a background-corrected Doppler spectrum $s_{Doppler}(f)$ by subtracting the background frequency spectrum $s_{bg}(f)$ from the frequency spectrum s(f). In some embodiments, the flowrate determination algorithm may include subtracting an average or median of the background-corrected Doppler spectrum data from the background-corrected Doppler spectrum to generate baseline corrected spectrum data for $f>f_{max}$, where $f_{max}=2*v_{max}/\lambda_0$, where $v_{max}$ is the highest expected flow velocity and where $\lambda_0$ is the laser wavelength. In some embodiments, the flowrate determination algorithm may include smoothing the baseline corrected data by averaging or applying a low pass filter and discarding frequency spectra data which are below zero or whose frequency are above fmax. In some embodiments, the flowrate determination algorithm may include calculating a first weighted moment from the spectral data. In some embodiments, the flowrate determination algorithm may include calculating a flow velocity based on a previously defined relationship of first moment and flow velocity.

In some embodiments, the one or more hardware processors may be configured to execute a flowrate determination algorithm. In some embodiments, the flowrate determination algorithm may include calculating frequency spectrum s(f) from a measured photodiode signal. In some embodiments, the flowrate determination algorithm may include subtracting a background frequency spectrum $s_{bg}(f)$ from the frequency spectrum s(f). In some embodiments, the flowrate determination algorithm may include calculating a baseline including an average or median of the background-corrected Doppler spectrum data. In some embodiments, the flowrate determination algorithm may include subtracting the baseline from the background-corrected frequency spectrum for frequencies greater than a threshold frequency. In some embodiments, the flowrate determination algorithm may include applying a lowpass filter to remove frequency spectrum data above the threshold frequency. In some embodiments, the flowrate determination algorithm may include calculating a first weighted moment from the filtered frequency spectrum data. In some embodiments, the flowrate determination algorithm may include calculating a flow velocity based on a relationship of first moment and flow velocity.

In some embodiments, the threshold frequency may be based on highest expected flow velocity and laser wavelength parameters. In some embodiments, the threshold frequency may include $f_{max}=2*v_{max}/\lambda_0$, where $v_{max}$ is the highest expected flow velocity, and where $\lambda_0$ is the laser wavelength. In some embodiments, the laser wavelength may be in a range of 390 nm to 750 nm. In some embodiments, the laser wavelength may be in a range of 640 nm to 750 nm. In some embodiments, the previously defined relationship of first moment and volumetric flowrate may be stored on the electronic storage memory medium of the MCS device. In some embodiments, the relationship of first moment and volumetric flowrate may be a linear relationship. In some embodiments, the relationship of first moment and volumetric flowrate may be a non-linear relationship.

In some embodiments, the one or more hardware processors may be configured to execute a computer operable algorithm for determining a volumetric flowrate of blood through the MCS device using Laser Doppler Velocimetry (LDV) based on first weighted moment of a power density spectra. In some embodiments, the relationship between the first weighted moment and the volumetric flowrate may be non-linear.

In some embodiments, the non-linear relationship may be stored on an electronic storage medium in the MCS device. In some embodiments, the relationship may be applied to the MCS device. In some embodiments, the non-linear relationship may be predetermined in a test scenario. In some embodiments, the test scenario may include a scenario where the MCS test device is in contact with a fluid medium including at least one of: still blood, a sterile medium having similar particles and scattering pattern to blood, and air.

In some embodiments, the test scenario may be conducted using the MCS device or a sample of one or more MCS devices from a manufacturing batch of MCS devices.

In some embodiments, the non-linear relationship may be stored in a form of an equation, extrapolation between data points, a lookup table, or a characteristic map. In some embodiments, the equation may include a high order polynomial equation. In some embodiments, the non-linear relationship may be represented by $Q=(k_0/k_{ges})*f_m$, where $k_0$ is the linear proportionality factor between $f_m$ and Q, and $k_{ges}=1+k1*e^{-k2*fm}$, where $f_m$ is the middle frequency of the used frequency range, and k1 and k2 are fitting parameters. In some embodiments, $k_{ges}$ may in the test scenario.

In some embodiments, the test scenario may include determining a reference data set. In some embodiments, the reference data set may be determined by delivering light to an optical fiber of a tested MCS device with a fluid medium flowing at known flowrates. In some embodiments, the reference data set may be determined by measuring a photodiode signal from light attenuated by the fluid medium. In some embodiments, the reference data set may be determined by calculating a power density spectrum from the measured photodiode signal. In some embodiments, the reference data set may be determined by dividing the power density spectrum into a plurality of test device frequency bins. In some embodiments, the reference data set may be determined by determining a factor, $k_{ges}$, to transform test device frequency bins to approximate a reference dataset. In some embodiments, $k_{ges}$ may be described by the function $k_{ges}=1+k1*e^{-k2*fm}$. In some embodiments, fm may be the middle frequency of the used frequency range. k1 and k2 may be fitting parameters.

In another aspect, a system for measuring fluid flow characteristics in a tube is described. The system for measuring fluid flow may include a tubular channel configured to flow fluid therethrough. The system for measuring fluid flow may also include a flow disturbance located on an inside surface of the tubular channel. The system for measuring fluid flow may include an optical measurement head protruding at least partially into the tubular channel downstream of the flow disturbance and configured to measure a parameter of disturbed flow at a boundary layer of the fluid flow.

In some embodiments, the optical measurement head may be an end of a light guide or an optical fiber facet or an optical window. In some embodiments, the system for measuring fluid flow may further include a plurality of the flow disturbances located upstream of the optical measurement head. In some embodiments, the flow disturbance may include a pin or ridge.

In some embodiments, the flow disturbance may protrude radially inwardly beyond the inside surface of the tubular channel a distance of hp. In some embodiments, the tube may have a radius R. In some embodiments, hp may be ≥0.1 R. In some embodiments, the flow disturbance may protrude radially inwardly beyond the inside surface of the tubular channel at a distance of hp. In some embodiments, the flow disturbance may have a width or diameter dp that is perpendicular to hp.

In some embodiments, a distance between the flow disturbance and the optical measurement head may be greater than dp. In some embodiments, the distance between the flow disturbance and the optical measurement head may be greater than 5×dp. In some embodiments, the distance between the flow disturbance and the optical measurement head may be greater than 10×dp.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated and make part of this disclosure.

DETAILED DESCRIPTION

Figure 1A:
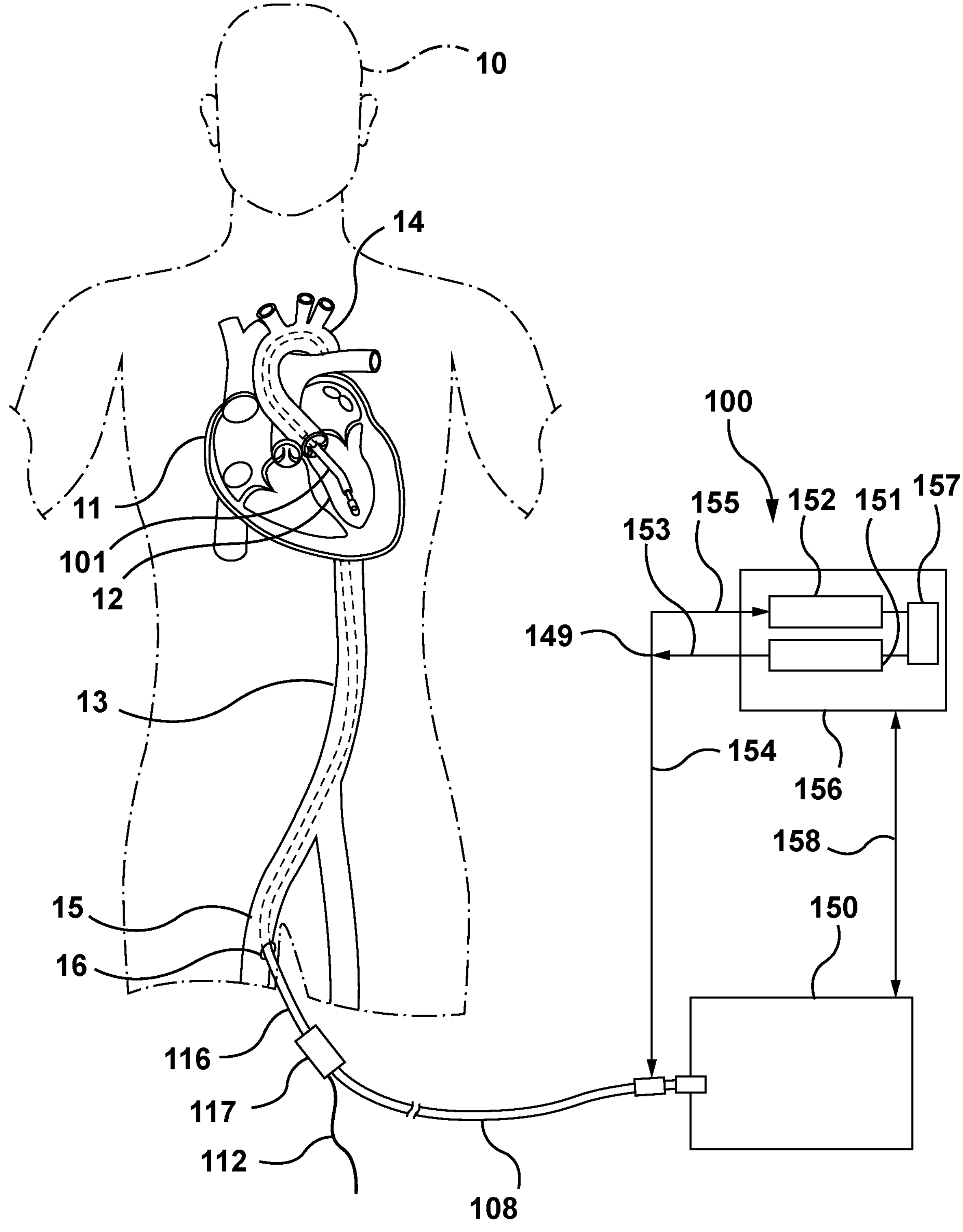
FIG. 1A is a schematic illustration of an example embodiment of a Laser Doppler Velocimetry (LDV) technique in the context of a Mechanical Circulatory Support (MCS) system.

The following detailed description is directed to certain specific embodiments. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings.

Various aspects relating to laser doppler-based analyses of fluid flows are described herein. While the techniques are described primarily in the context of cardiac mechanical circulatory support (MCS) systems, the laser doppler techniques may be used in other contexts, such as non-medical applications to determine flow velocity of fluids, optical scatterers, as well as distribution of flow velocity with respect to distance of scatterers from a light-emitting and light-receiving surface of a fiber.

There remains a need for fluid flow analysis systems that accurately and reliably measure fluid flow parameters such as velocity and volumetric flow. Such a system can be used with heart pump systems to measure cardiac output accurately and reliably, which may include output of the pump, natural output, or a combination of both. The disclosure herein is related to components for conducting Laser Doppler Velocimetry (LDV) to measure volumetric flow of blood. One example application of such a system can include measuring fluid flow through a MCS device or through an aortic valve around an implanted MCS device.

Laser Doppler Velocimetry (LDV) is a technique of using a Doppler shift in a laser beam to measure velocity in transparent or semi-transparent fluid flows. The general technique of LDV involves directing coherent light towards particles whose velocity is to be measured. The light is scattered by the particles to be measured and experiences a Doppler (or frequency) shift. The frequency shift depends on a velocity vector of the particles and the light propagation direction. The scattered light may interfere with light reflected by immobile objects, such as an edge of a fiber configured to direct the coherent light. As a result, a pulsation may be observable in a photodiode capturing this light. The pulsation may have a frequency as large as the Doppler shift. A frequency spectrum of the pulsations, such as a power spectrum, can be calculated from the amplified and numerically converted time dependent photodiode signal by a Fourier analysis, or other numerical techniques. From this frequency spectrum, a velocity or velocity distribution can be obtained. For flow in a pipe, velocity is related to volume flow. In an example MCS device application for a LDV technique, a flow in a pipe may serve as an approximation to an inlet cannula of the MCS device.

In some embodiments, an LDV technique may cross two beams of collimated, monochromatic, and coherent laser light in a flow of the fluid being measured. The two beams may be obtained by splitting a single beam of light, thus ensuring coherence between the resulting two collimated beams. Lasers with wavelengths in the visible spectrum (390-750 nm) may optionally be used, allowing a beam path to be observed. For example, one or more lasers that can be used in an LDV system may include, but are not limited to, He—Ne, Argon ion, or laser diode. Transmitting optics may focus the beams to intersect at their waists (or the focal point of a laser beam), where they interfere and generate a set of straight fringes. As particles in the fluid (e.g., blood cells) pass through the fringes, the particles reflect light that may then be collected by receiving optics and focused on a photodetector (e.g., a camera or other imaging sensor). The frequency of fluctuations in intensity of the reflected light is equivalent to the Doppler shift between the incident and scattered light and is thus proportional to the component of particle velocity which lies in a plane of the two laser beams. If the sensor is aligned to the flow such that the fringes are perpendicular to the flow direction, an electrical signal from the photodetector will then be proportional to a full particle velocity.

Some embodiments of the LDV technique may involve an approach that may be similar to an interferometer. A sensor may split a laser beam into two parts: one (a measurement beam) is focused into a flow and the second (a reference beam) does not pass through the flow but is sent to a photodetector. Receiving optics provide a path that intersects the measurement beam, forming a small volume. Particles passing through this volume will scatter light from the measurement beam with a Doppler shift, and a portion of this light is collected by the receiving optics and transferred to a photodetector. The reference beam may also be sent to the photodetector where optical heterodyne detection may produce an electrical signal proportional to the Doppler shift, by which the particle velocity component perpendicular to a plane of the beams can be determined. It may be possible to apply digital techniques to the signal to obtain the velocity as a measured fraction of the speed-of-light.

Some embodiments of the LDV technique may involve a single laser beam being emitted into blood flowing through a space of known dimensions (e.g., an inlet tube of an MCS device). The light gets scattered off of moving blood cells. The scattered light experiences a Doppler (or frequency) shift, which approaches zero if a direction of blood or other fluid and the k-vector of light are perpendicular and has a maximum if the direction of blood or other fluid and the k-vector of light are parallel to each other. A k-vector may also be referred to as a wave vector, which includes the magnitude and direction of light. The light scattered off of moving blood cells (or other particulates) may interfere with light scattered off of immobile objects, such as an edge of a fiberoptic or an edge of an inlet tube of an MCS device. As a result, an interference pulsation may be observable in a photodiode capturing the scattered light. Captured light may be directed through a receiving optical fiber that passes through a catheter (for example, of the MCS device) to a photodiode in an LDV module (that may, for example, be external to a patient whose blood flow is being measured or other source of flow). The receiving optical fiber may be a different fiber than the transmitting fiber in which case the receiving fiber may send the received light to a photodiode. Alternatively, a single transmitting and receiving fiber may direct received light back to a laser source where the laser is modulated.

FIG. 1A shows an LDV module 156 in the context of an example mechanical circulatory support (MCS) system 100. In the illustrated example, an LDV module 156 includes a laser source 151 and a photodiode 152. The LDV module 156 may be associated with electronics to drive both the laser source 151 and photodiode 152 and a data evaluation module 157, for example, one or more hardware processors or a Field Programmable Gate Array (FPGA). The LDV module 156 may be a separate system component that may not be contained in a control console 150. In some examples, fiber optics may connect the LDV module 156 to fiber optics in a connector cable 108. The LDV module may be configured to communicate with the control console 150 via a communication link 158, such as a connector cable or wireless connection. In some embodiments, a single optical fiber 154 may run through the connector cable 108 and may be connected to the laser source 151 and the photodiode 152 by a Y-splitter 149. The optical fiber 154 may be split into a source fiber 153 and a return fiber 155 by the Y-splitter 149. In some examples, one or more laser delivery fibers and one or more return fibers may be incorporated into the connector cable 108. In some embodiments, the LDV module 156 may be contained and integrated in the control console 150.

In some embodiments, (such as illustrated in FIG. 1A) a receiving fiber for collecting backscattered light may be the same fiber as a transmitting fiber. In the illustrated example, a Y-splitter 149 may be incorporated into a cabling system that may, when used in context of an MCS system 100, be external to a patient's body or, in another embodiment, external to another source of fluid flow. The Y-splitter 149 may be configured to passively separate transmitted light from received light and direct the received light to a photodiode 152, which may be done, for example, with a one-way mirror. Advantageously, this Y-splitter configuration may have a benefit of being passive and simpler than other configurations. In this Y-splitter configuration, pulsation may have a frequency directly corresponding to a Doppler shift. Pulsation frequency may be obtained, for example, by standard Fourier analysis. From this frequency, a velocity or velocity distribution may be obtained. With a known diameter of a space (e.g., inlet tube or blood vessel) within which measurement takes place, volumetric flow rate may be obtained.

With the use of a Laser Doppler Velocimetry (LDV) technique, and with a defined size of an inlet tube, precise measurement of velocity of blood or other fluid or volume flow within an MCS Device or other device is possible. Collected signals (e.g., electromagnetic waves or light waves) may be transmitted via optical fibers. Advantageously, optical fibers may help avoid distortion of electrical signals by environmental influences, such as motor drive current, mechanical vibrations of a motor, or other electrical signals. Such environmental influences may be disadvantageous, for example, in measuring blood flow rate in an MCS device by means that require transmission of electrical signals.

It shall be understood that for the various configurations and embodiments disclosed herein there can be one or more optical fibers that can be single- or multi-core and the optical fibers do not need to be continuous between a controller and a device but can be joined together with standard optical fiber connections. Laser light may be transmitted having various wavelengths or power.

Figure 1B:
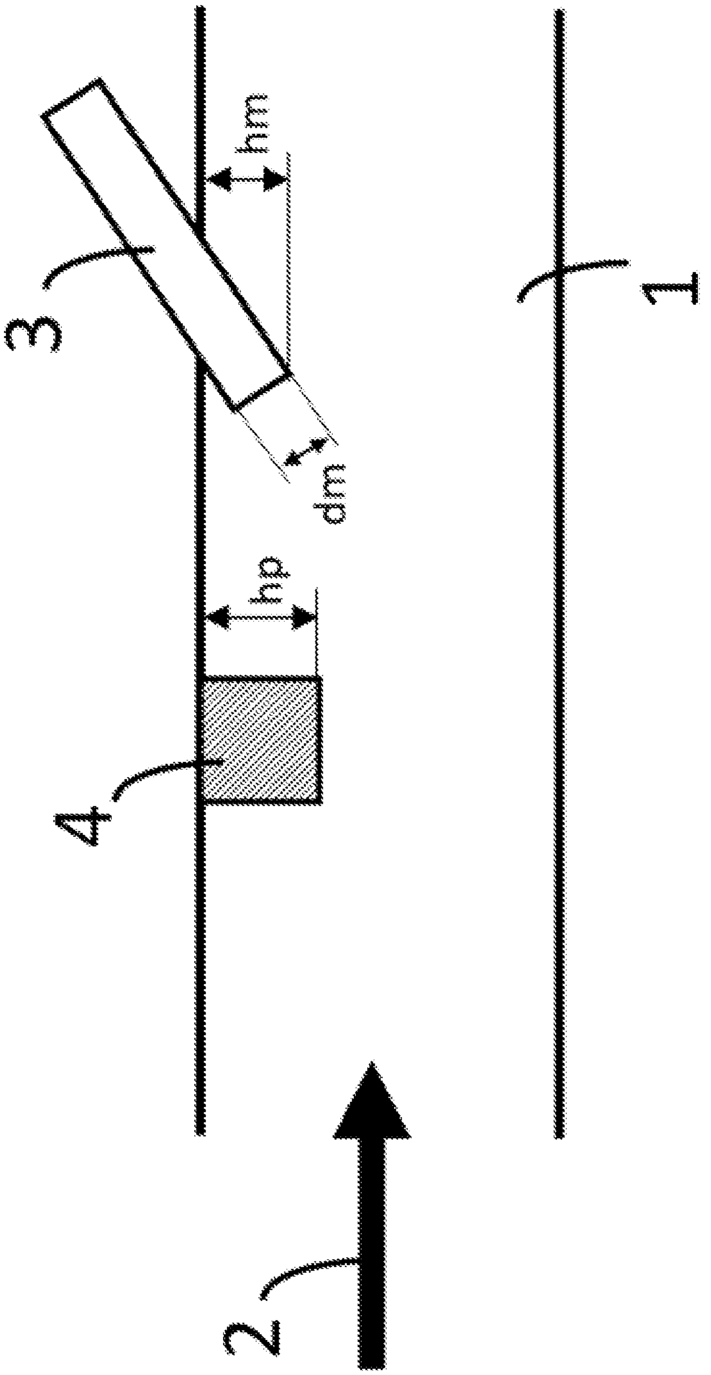
FIG. 1B is a schematic illustration of an example LDV system for measuring flow of fluids in a tube geometry.

Example Configuration of a Laser Doppler Velocimeter System for Measuring Fluid Flow FIG. 1B shows an example configuration of a Laser Doppler Velocimeter (LDV) system. The LDV system may be configured to measure a tube flow 2 of fluids. Fluids may include heterogeneous mixtures that contain optically scattering substances, including but not limited to, suspensions (such as, for example, wheat beer), emulsions (such as, for example, milk), aerosols (such as, for example, smoke), foam, and the like.

The LDV system illustrated in FIG. 1B may include a tube 1 into which a measurement head 3 may extend. The measurement head 3 may include an end of a light guide (not shown) or an optical fiber facet (not shown) or optical window (not shown). The system may include one or more objects 4 disposed in the tube 1 so as to remain fixed with relation to the measurement head 3. The one or more objects 4 may disturb a flow of fluid flowing through the tube 1. The one or more objects 4 may include a structure configured to disrupt a flow pattern of the fluid in the tube, including but not limited, to a pin or a ridge. The size, shape, and/or positioning of the one or more objects 4 may be of a sufficient size, shape, and/or position to cause a perceivable change in flow at or by the measurement head 3. The parameters of the one or more objects 4 may be dependent and/or may be correlated with the parameters of the tube 1 and/or measurement head 3. In some embodiments, the one or more objects 4 may have a width or diameter dp>0.2 mm. However, other sizes are also possible. In some embodiments, the one or more objects 4 may extend perpendicular from a wall of the tube 1. In some embodiments, a height hp of the one or more objects 4 from the base of the wall of the tube 1 may be at least as long as the measurement head (hm). In some embodiments, the height hp of the one or more objects 4 may be correlated with an inner radius R of the tube 1 in the vicinity of the measurement head 3 such that: hp≥0.1 R.

A distance between the measurement head 3 and one or more objects 4 in a flow direction 2 may be in the range of 1 to 15 times dp upstream of the measurement head 3. This orientation may lead to a flow disturbance in a boundary layer of the tube flow superimposed on a flow disturbance caused by the measurement head 3 and may make a measurement result of the fluid flow more reliable.

For measurement of turbid media, an LDV system may be preferably equipped with a laser source 151 with at least one probe wavelength which has greater effective penetration depth to=1/alphaeff, where alphaeff is the effective attenuation coefficient in a light scattering absorbing medium, than:

$$\text{to} \geq 12 * \sqrt{\frac{dm * nu}{vmin}},$$

where dm is a width or diameter of the measurement head 3, nu is the kinematic viscosity of the fluid, and vmin is the lowest velocity to be measured.

Figure 1C:
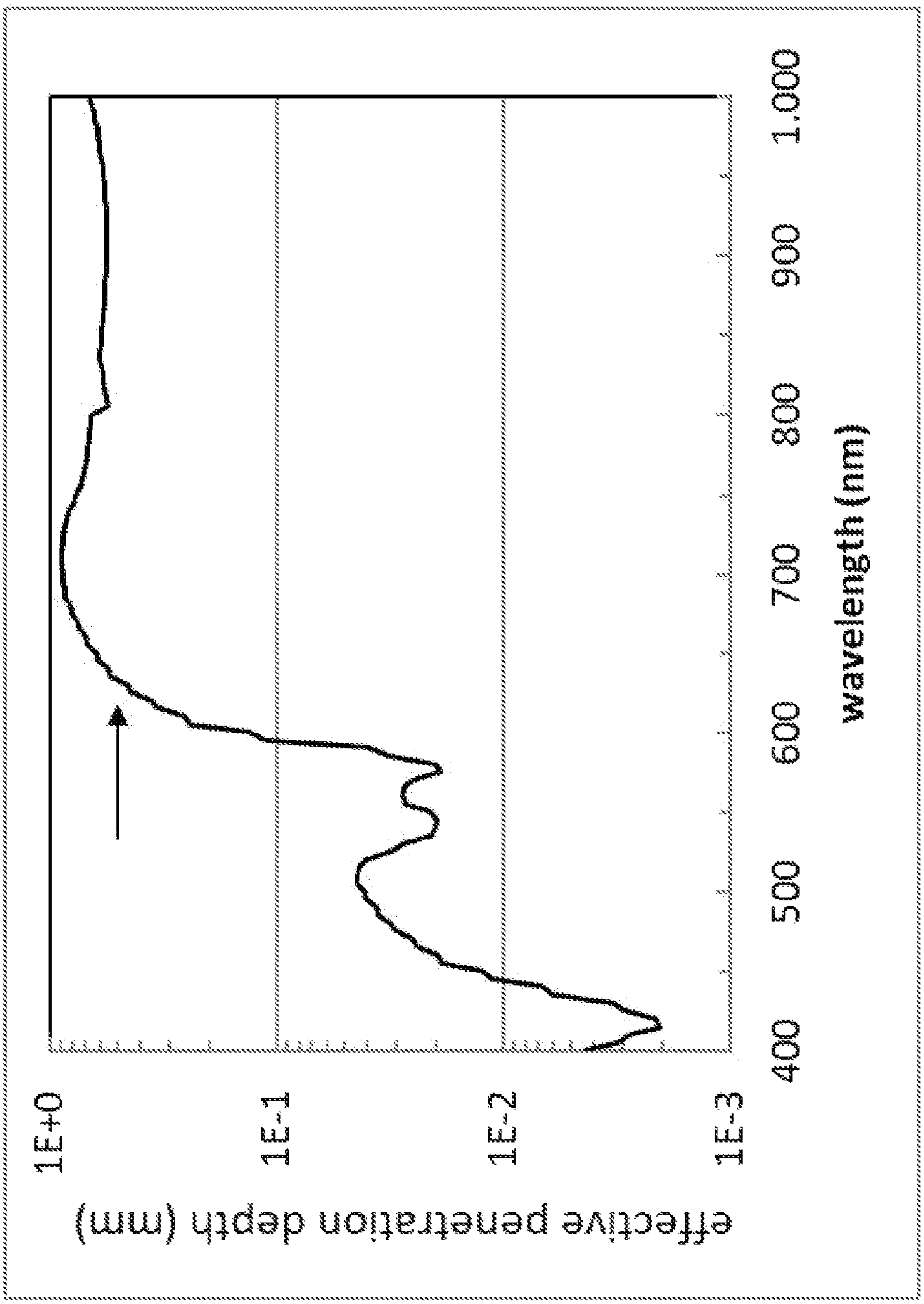
FIG. 1C is a plot of a relationship between effective penetration depth of light into oxygenized blood and wavelength of that light.

FIG. 1C shows an example plot of a relationship between effective penetration depth of light into oxygenized blood and wavelength of that light. For example, for an optical fiber facet used as a sensor head 3 and with a diameter dm=300 μm diameter, to measure flow velocities larger than vmin=0.5 m/s in blood (nu=$2.8\times10^{-6}$ $m^2/s$), an effective penetration depth to of the light into the blood should be greater than 0.5 mm. For blood, this effective penetration depth to of a light may be possible with a wavelength above 640 nm, as shown by the arrow marker in FIG. 1C.

Example Application of a Laser Doppler Velocimeter (LDV) Technique in a Mechanical Circulatory Support (MCS) System MCS systems are used to unload the burden on a patient's heart by contributing to cardiac output with a pump mechanism. For example, if a patient's heart is at risk of or is insufficiently perfusing the patient's organs, an MCS system may be used to raise cardiac output to a more desirable level. Cardiac output may be measured for clinical evaluation of a patient's state of health. Cardiac output may also be measured to evaluate function of the MCS device. In the context of MCS devices, cardiac output is composed of a natural output provided by a patient's heart in addition to the output of a MCS system pump. A degree of support may be described as the proportion of a volume flow conveyed by the pump of the MCS system to a total volume flow of blood from a ventricle to an aorta. Cardiac output or total volume flow from a ventricle to an aorta is therefore usually a sum of the pump volume flow ($Q_P$) and the aortic valve volume flow ($Q_A$).

One approach for measuring pump volume flow ($Q_P$) may include correlating flow to operating parameters of the MCS system, such as the electrical power consumed by an MCS's electrical motor, and possibly supplemented by other physiological parameters such as blood pressure. An example of this established approach is disclosed in U.S. Pat. No. 10,765,791, entitled DETERMINATION OF CARDIAC PARAMETERS FOR MODULATION OF BLOOD PUMP SUPPORT, issued Sep. 8, 2020. However, this indirect measurement by the motor current draw or power consumption may be imprecise and/or flawed. Furthermore, effects of viscosity of the medium or pressure head are determined externally or via models which can only approximate the true flow rate. Still further, increases or decreases of the motor current may be influenced by a multitude of unrelated parameters, such as wear, heart volume, pressure head, suction events, or viscosity.

Integration of dedicated ultrasound or temperature measurement technology into a support system for measuring pump volume flow has previously been proposed by Kardion GmbH in German Patent App. No. DE102014221495, entitled ULTRASONIC TRANSDUCER, ULTRASONIC FLOWMETER AND METHOD OF MANUFACTURING AN ULTRASONIC TRANSDUCER, filed Oct. 23, 2014, International Patent Pub. No. WO2020/064707, entitled METHOD AND SYSTEM FOR DETERMINING A FLOW SPEED OF A FLUID FLOWING THROUGH AN IMPLANTED, VASCULAR ASSISTANCE SYSTEM, published Apr. 2, 2020, International Patent Pub. No. WO2019/234163, entitled METHOD AND SYSTEM FOR DETERMINING THE SPEED OF SOUND IN A FLUID IN THE REGION OF AN IMPLANTED VASCULAR SUPPORT SYSTEM, published Dec. 12, 2019, International Patent Pub. No. WO2019/234164, entitled METHOD FOR DETERMINING A FLOW RATE OF A FLUID FLOWING THROUGH AN IMPLANTED VASCULAR SUPPORT SYSTEM, AND IMPLANTABLE VASCULAR SUPPORT SYSTEM, published Dec. 12, 2019, International Patent Pub. No. WO2019/234166, entitled METHOD FOR DETERMINING A FLOW SPEED OF A FLUID FLOWING THROUGH AN IMPLANTED, VASCULAR ASSISTANCE SYSTEM AND IMPLANTABLE, VASCULAR ASSISTANCE SYSTEM, published Dec. 12, 2019, International Patent Pub. No. WO2019/229220, entitled INTRAVASCULAR BLOOD PUMP AND METHOD FOR PRODUCING ELECTRICAL CONDUCTOR TRACKS, published Dec. 5, 2019, International Patent Pub. No, WO2019/234146, entitled LINE DEVICE FOR A VENTRICULAR ASSIST DEVICE AND METHOD FOR PRODUCING A LINE DEVICE, published Dec. 12, 2019, International Patent Pub. No. WO2019/234149, entitled SENSOR HEAD DEVICE FOR A MINIMAL INVASIVE VENTRICULAR ASSIST DEVICE AND METHOD FOR PRODUCING SUCH A SENSOR HEAD DEVICE, published Dec. 12, 2019, International Patent Pub. No.

WO2019/234151, entitled IMPLANTABLE DEVICE FOR DETERMINING A FLUID VOLUME FLOW THROUGH A BLOOD VESSEL, published Dec. 12, 2019, International Patent Pub. No. WO2019/234152, entitled DEVICE AND METHOD FOR DETERMINATION OF A CARDIAC OUTPUT FOR A CARDIAC ASSISTANCE SYSTEM, published Dec. 12, 2019, and International Patent Pub. No. WO2020/030686, entitled IMPLANTABLE VASCULAR SUPPORT SYSTEM, published Feb. 13, 2020, the entire contents of each of which is hereby incorporated by reference herein for all purposes and forms a part of this specification. However, flow measurement from ultrasound, doppler or thermal techniques may require transmission of analog or digital signals through conductors that are in close proximity to conductors that provide power to a pump motor, which may potentially cause degradation of the signals or prevent a measurement altogether.

Integration of dedicated electrical impedance measurement technology into a support system for measuring ventricular volume or pump volume flow has previously been proposed by Kardion GmbH in International Patent Pub. No. WO2019/234148, entitled IMPLANTABLE VENTRICULAR ASSIST SYSTEM AND METHOD FOR OPERATING SAME, published Dec. 12, 2019 and International Patent Pub. No. WO2019/234148, entitled IMPLANTABLE VENTRICULAR ASSIST SYSTEM AND METHOD FOR OPERATING SAME, published Dec. 12, 2019, each of which is hereby incorporated by reference herein in its entirety for all purposes and forms a part of this specification.

Blood flow rate may also be used in the calculation of blood viscosity, which may be a clinically relevant measure. An example of calculating blood viscosity using blood flow rate is described by Kardion GmbH in International Patent Pub. No. WO2019/234167, entitled DETERMINATION APPLIANCE AND METHOD FOR DETERMINING A VISCOSITY OF A FLUID, published Dec. 12, 2019, and International Patent Pub. No. WO2019/234169, entitled ANALYSIS APPARATUS AND METHOD FOR ANALYZING A VISCOSITY OF A FLUID, published Dec. 12, 2019, each of which are hereby incorporated by reference herein in their entirety.

Blood flow rate may also be used in the assessment of device wear or functionality, such as described, for example, by Kardion GmbH in International Patent Pub. No. WO2019/243582, entitled METHOD AND DEVICE FOR DETECTING A WEAR CONDITION OF A VENTRICULAR ASSIST DEVICE AND FOR OPERATING SAME, AND VENTRICULAR ASSIST DEVICE, published Dec. 26, 2019, which is hereby incorporated by reference herein in its entirety.

All publications and patent applications mentioned in this specification are herein incorporated by reference to the same extent as if each individual publication or patent application was specifically and individually indicated to be incorporated by reference. Any feature of any reference incorporated by reference herein may be used in combination with any of the systems, devices, and methods described herein, and vice versa. In case of any discrepancy or conflict between the current disclosure and any reference incorporated by reference, the current disclosure supersedes such discrepancy or conflict.

As further shown in FIG. 1A, the MCS system 100 may use the LDV techniques described herein and be configured to measure volumetric flow rate of blood flowing through and/or around an MCS device 101 implanted at least partially in a patient's heart 11 (e.g., an inlet portion of the MCS device may be positioned in a left ventricle 12 and an outflow portion of the MCS device may be positioned in the aorta 13) and optionally delivered and connected through natural vasculature (e.g., via access at a femoral artery 15, or other vascular access point such as a carotid artery, subclavian artery, or radial artery). The connection through the natural vasculature may be via a catheter 116. The catheter 116 may be configured to include communication components and/or some combination thereof, such as electrical conductors and laser conductors (e.g., optical fibers, coaxial optical fibers, single core optical fibers, multicore optical fibers) and, optionally, a guidewire lumen through which a guidewire 112 may be positioned to assist placement of the MCS device or other catheterization steps. The catheter 116 may have a proximal hub 117 that optionally has a guidewire outlet in communication with the guidewire lumen, and a connector configured to connect a connecting cable 108. In the illustrated example, the connecting cable 108 is shown connecting the catheter 116 of the MCS device 101 implanted in the body to a control console 150 located outside the body 10. As noted above, the control console 150 may contain or may communicate with an LDV module 156 which includes a laser source 151, a photodiode 152 and electronics to drive both and a data evaluation module 157, for example, one or more hardware processors or an FPGA. The LDV module 156 may be a separate system component that is not physically contained in the control console 150. In some embodiments, fiber optics may connect the LDV module 156 to fiber optics in the connector cable 108. The LDV module may be configured to communicate with the control console 150 via a communication link 158, such as a connector cable or wireless connection. In some embodiments, a single optical fiber 154 may run through the connector cable 108 and may be connected to a laser source 151 and a photodiode 152 by a Y-splitter 149. The optical fiber 154 may be split into a source fiber 153 and a return fiber 155 by the Y-splitter 149. In some embodiments, one or more laser delivery fibers and one or more return fibers may be incorporated into the connector cable 108. In some embodiments, the LDV module may be contained and integrated in the control console 150.

Figure 2:
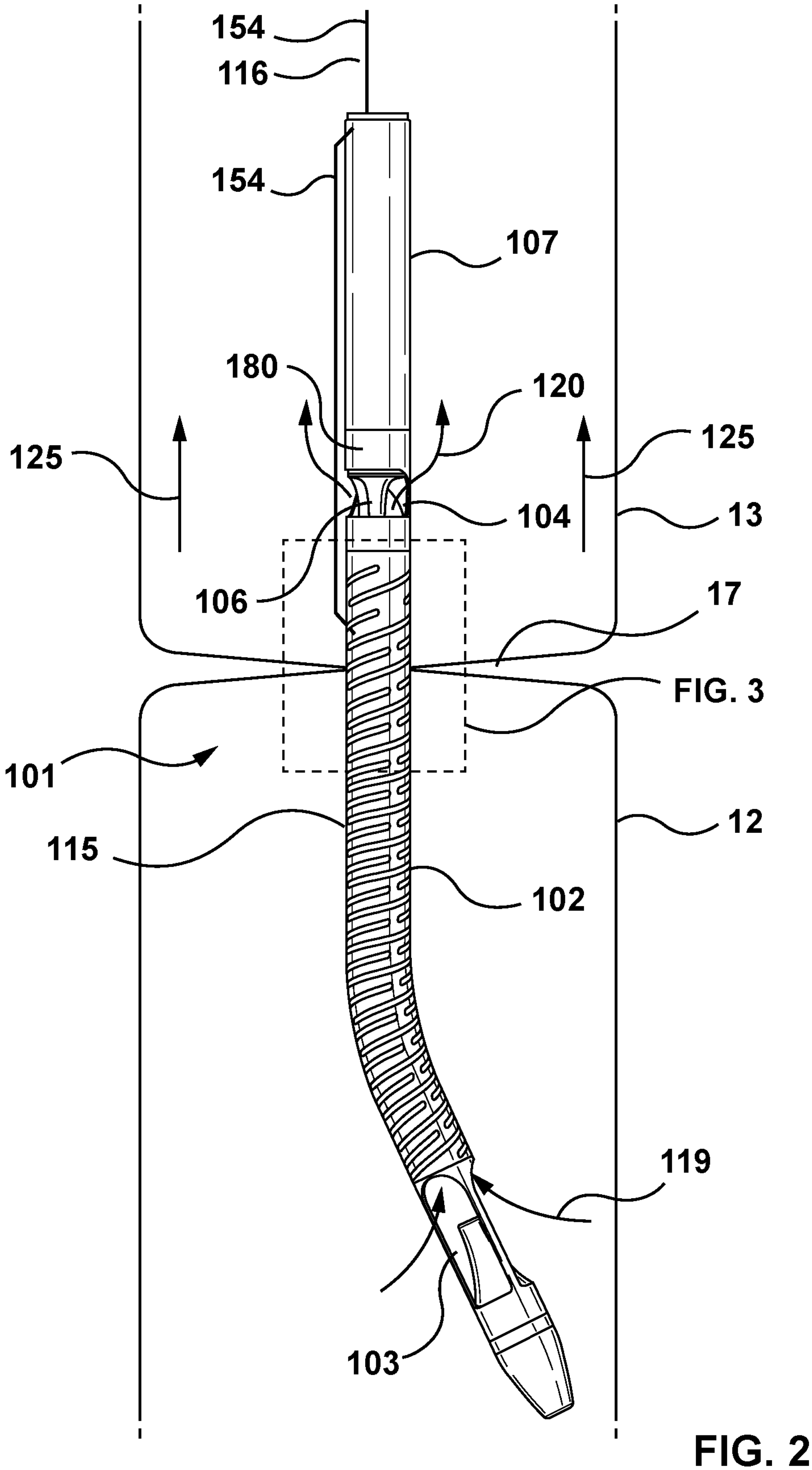
FIG. 2 is a schematic illustration of an example MCS device in situ configured for LDV analysis of blood flowing through the device.

FIG. 2 shows a closer view of the example MCS device 101 of FIG. 1A that may be implanted in a patient's heart 11 and aorta 13 that uses various LDV techniques described herein. The MCS device 101 is shown placed across the aortic valve 17 via a single femoral arterial access (see FIG. 1A). The MCS device 101 may include a pump 115 mounted on a catheter 116. The MCS pump 115 may be a low-profile axial rotary blood pump. The catheter 116 may have a smaller outer diameter (e.g., in a range of 6 French (Fr) to 12 Fr, preferably 8 Fr) than a diameter of the MCS pump 115 (e.g., in a range of 12 Fr to 21 Fr, preferably 14 to 18 Fr), where 1 Fr=⅓ millimeter (mm). When in place, the MCS pump 115 may be powered, for example, by the MCS control console 150. The MCS control console 150 may be configured to turn a motor 107 in the MCS pump 115. The motor 107 may be configured to turn an impeller 106 that may draw blood through an inlet cannula 102. In some embodiments, the motor 107 may be an axial rotary motor or other motor type capable of turning an impeller to draw blood through a channel or cannula. Blood may enter the inlet cannula 102 from a first anatomical location, such as the left ventricle 12, through one or more inlet windows 103 as shown by flow arrows 119 and may leave the inlet cannula through one or more outlet windows 104 as shown by flow arrows 120 to a second anatomical location, such as the aorta. The MCS pump 115 may provide a flow of blood to at least partially support natural function of a patient's anatomy such as the patient's heart or components of the heart such as the left ventricle. The flow of blood may be in a range of up to and including approximately 6.0 liters/minute (e.g., up to 4.0 liters/minute). The volumetric flow rate of blood flowing 118 through the inlet cannula 102 is of particular clinical interest and may be a target measurement of an LDV system described herein. Optionally, an LDV system may measure the volumetric blood flow 125 through a portion of the patient's vasculature around the MCS pump 115 in addition or alternative to flow 118 through the inlet cannula 102.

The inlet cannula 102 may be adapted to be elastically flexible so it can pass through vascular bends during delivery and removal of the system to and from the body of a patient. In addition, the inlet cannula 102 may be configured to return to its unconstrained shape when placed in a target anatomy. The inlet cannula 102 may also have sufficient hoop strength to resist collapsing when the impeller 106 is activated to draw blood through the inlet cannula. For example, the inlet cannula 102 may be made from a laser cut elastically flexible tube 123 (not shown) (e.g., made from Nitinol) with a flexible membrane layer 124 (not shown) to seal the laser cuts and allow blood to flow only through the one or more inlet windows 103 or the one or more outlet windows 104. An optical fiber 154 may be positioned in the catheter 116 and may be connected to the LDV module 156 via an optional extension cable and connectors. Optionally, the optical fiber 154 may terminate at a connection module located between the catheter 116 and the MCS pump 115, and a separate optical fiber 154' may connect to the connection module and continue to a light transmission position, for example in the inlet cannula 102, to facilitate manufacturing. For simplicity, FIGS. 2, 5, 6 and 7 illustrate the optical fiber 154' schematically. Optical fibers may be firmly coupled to the MCS pump 115. In some embodiments, the optical fibers may be coupled to the MCS pump 115 with, for example, adhesive. In some embodiments, the optical fibers may be embedded in a substrate layer that is coupled (e.g., glued) to a surface of the MCS pump 115. In some embodiments, the optical fibers may be contained under a membrane layer surrounding a structural layer, passing through a lumen or channel in the MCS pump 115. In some embodiments, the optical fibers may be coupled to or connected to the MCS pump 115. In some embodiments, one or more optical fibers may be connected to an exterior surface of housing of the motor 107, an outflow strut 121 that may partially define one or more outlet windows 104, and/or along the inlet cannula 102, optionally in a coiled pattern that follows a pitch of laser cuts, which may allow the inlet cannula 102 to remain flexible. An example of a pathway for an optical fiber 154' is shown in FIG. 7, wherein a distal end of the optical fiber 154' terminates in a distal nose piece 114. Optionally, the distal end of the optical fiber 154' may terminate in other locations such as within the inlet cannula 102 between the one or more inlet windows 103 and the one or more outlet windows 104, optionally distal to the impeller 106.

Figure 3:
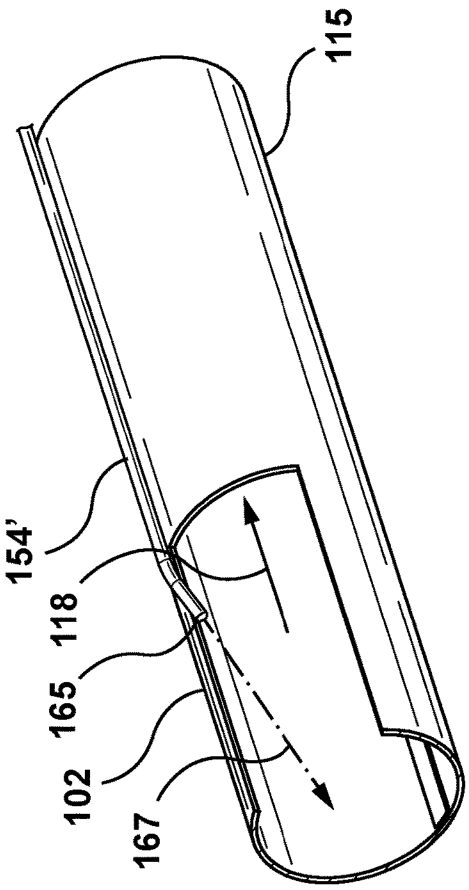
FIG. 3 is a partial cutaway view of a section of the device of FIG. 2.

FIG. 3 shows a cutaway closeup view of a portion of the inlet cannula 102 of FIG. 2, wherein the inlet cannula 102 is simplified and shown as a solid cylindrical tube. The configuration of the inlet cannula 102 may not be limited to the configuration shown. FIG. 3 illustrates a configuration of an LDV system having a single optical fiber 154' integrated in to the MCS pump 115. A distal terminating tip 165 of the fiber 154' may direct a laser beam provided by a laser source 151 into a lumen within the inlet cannula 102. The inlet cannula 102 may be at a known angle in relation to the inlet tube's central axis 166 or tubular wall or a particular region of flow through the inlet tube. Optionally, the laser may be aimed at or through a region of flow within the inlet tube that is modeled to have a particular flow characteristic such as laminar flow, average flow, maximum flow, or turbulent flow. Optionally, turbulence may be created or manipulated in a region of flow where the laser is aimed to produce sufficient backscatter, which may be particularly beneficial if a terminal end of the optical fiber is positioned in the device in a location where flow may be too laminar to cause sufficient backscatter. For example, one or more flow affecting features may be positioned on the device upstream of the focal region, such as in the inlet tube or in the one or more inlet windows 103. Optical fibers, which may be made of glass or other transparent material, such as a crystalline material (e.g., sapphire), have a minimum bending radius (e.g., mm for a fiber having a diameter of about 245 micrometers), which may be a factor in how the distal terminating tip of the optical fiber is configured inside the tube. For example, the distal terminating tip 165 of the optical fiber 54 may be formed such that the flow 118 inside the cannula is not sufficiently disturbed and no sharp edges are present to significantly affect fluid flow or hemolysis. The distal terminating tip 165 of the optical fiber may be shaped or may have a shaped component connected to it that is chosen (e.g., with the assistance of fluid modeling and bench tests) to minimize its effect on hemolysis or pump efficiency.

Figure 4:
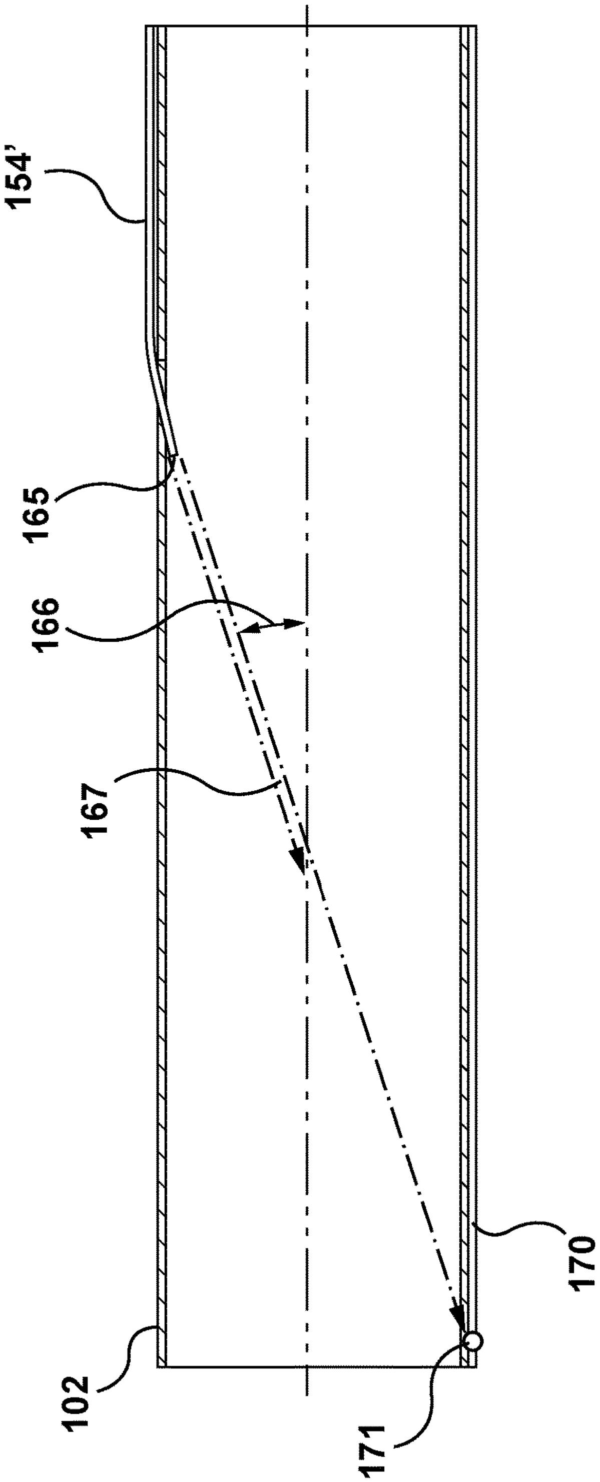
FIG. 4 is a cross-sectional view of a portion of the device of FIG. 3.

FIG. 4 shows a cross-sectional view of a portion of inlet cannula 102 of a configuration of an LDV system having a transmitting optical fiber 154' and a separate receiving fiber 170. A second optical fiber acting as the receiving fiber 170 may be positioned with its distal terminating tip 171 on an opposing side of the inlet cannula 102 in line with a transmitted laser beam 167. A micro-optic prism (not shown) or lens (not shown) connected to the distal terminating tip 171 of the receiving fiber 170 may be used to reflect or amplify received light into the receiving fiber 170. Alternatively, the distal terminating tip 171 of the receiving fiber 170 may be positioned proximal to the distal terminating tip 165 of a sending fiber 154'. A micro-optic prism (not shown) or lens (not shown) may be positioned with respect to the distal tip 165 of the sending fiber 154' to modify a direction of a beam emitted in a distal direction to aim it proximally toward the distal terminating tip 171 of the receiving fiber 170. With this configuration, when a second fiber 170' is incorporated, a y-splitter 149 is not required to separate transmitted laser from received light.

Figure 5:
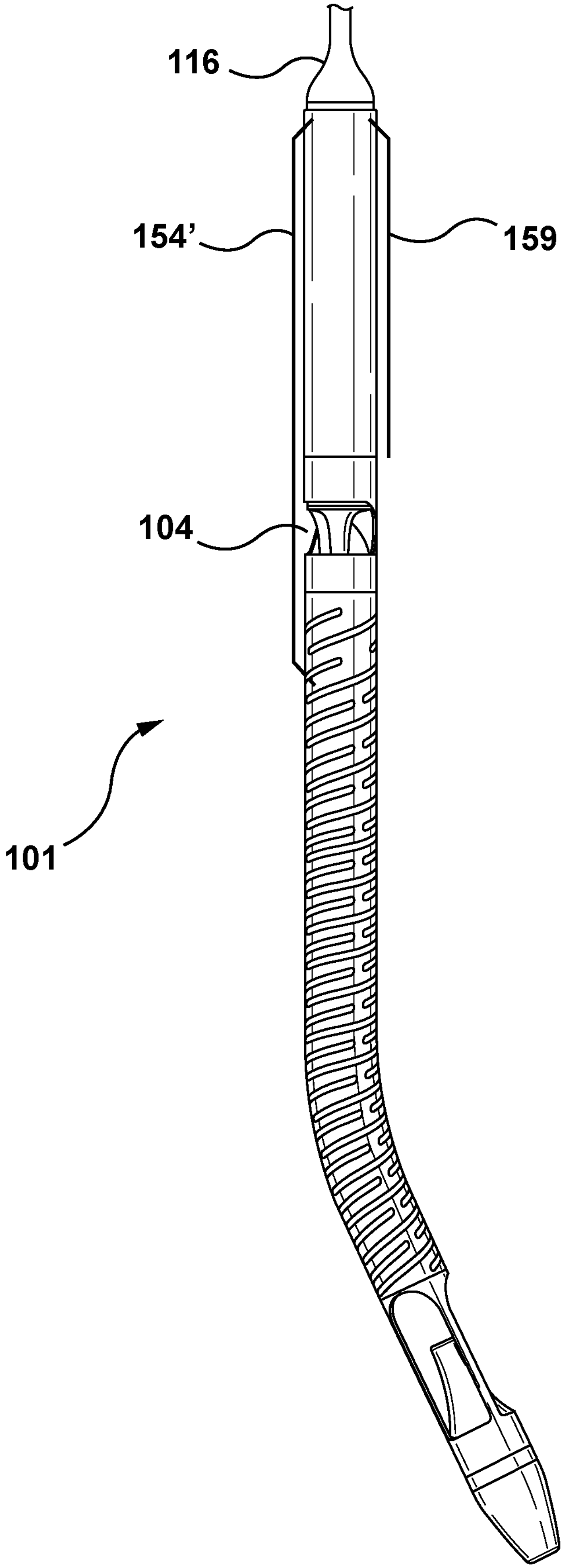
FIG. 5 is a side view of an example MCS device having a first fiber optic positioned to measure flow through an inlet tube and a second fiber optic positioned to measure flow around the device.

Optionally or alternatively, an LDV measurement may be taken by a fiber directing a laser to an area in the vasculature around the MCS pump 115 or catheter 116. The area may be, for example, either proximal to the one or more outlet windows 104 where blood flow includes a combination of blood flow 118 through the inlet cannula 102 and blood flow 125 driven by the pumping left ventricle 12 through the aortic valve 17 around the MCS pump 115; or distal to the one or more outlet windows 104 in a region occupied predominantly by blood flow 125 driven by the pumping left ventricle 12 through the aortic valve 17 around the MCS pump 115. For example, a fiber 159 is shown in FIG. 5 with its terminating tip positioned proximal to the outlet windows 104. This may optionally be in addition to the fiber 154' aimed into the inlet cannula 102, wherein both the flow through the MCS pump 115 and the flow external to the MCS pump, such as the flow 125 pumped by the left ventricle 12 through the aortic valve 17 or a combination of this and the flow 120 exiting the MCS pump, may be measured by the LDV module 156 and displayed on a user interface, for example, as numerical data or in a plot vs time.

Optionally, flow measurements in multiple locations or of multiple flow components may be used by an algorithm, operated by a controller of the LDV system, to generate warnings, alerts or procedural guidance to a user. A controller may include, but is not limited to, one or more hardware processors in communication with the one or more components of the LDV system 156, MCS device 101, or other device in communication with the LDV system 156. The controller may be part of the LDV system 156 or MCS device 101, or separate from the LDV system 156 or MC S device 101. The controller may be configured to receive an LDV measurement or signal, process the measurement or signal, and generate an output, such as a control signal, alert, or other output associated with an LDV measurement. For example, if a ratio of natural flow 125 to pumped flow 120 decreases over a threshold period of time (e.g., one day or a threshold number of hours or minutes), a controller could generate a user message related to the patient's recovery or health status. Optionally, in a system where an LDV measurement is taken proximal to the outlet windows 104 and wherein the impeller 106 is controlled to deliver continuous flow, a controller may determine how much of the flow is pulsatile compared to continuous. A pulsatile flow may represent the natural flow pumped by the left ventricle while a continuous flow may represent the flow pumped by the MCS device. The ratio of pulsatile flow to continuous flow over time may be an indicator of the patient's health or a factor in changing the flow rate of the MCS device 101. An increasing ratio may indicate a recovering heart while a decreasing ratio may indicate a worsening condition.

Optionally, flow data gathered by LDV measurements may be used to determine if the MCS device 101 is positioned correctly. A correct position, may, for example, involve the outlet windows 104 being positioned in the aorta 13 and the inlet windows 103 being positioned in the left ventricle 12. A controller may be configured to compare a pulsatility of flow or other measured flow data to expected pulsatility of flow or other measured flow data. For example, while the pump is operating, a controller may compare a measured pulsatility of flow to an expected pulsatility in flow. If the measured pulsatility is lower than a threshold or percentage of the expected pulsatility, the controller may determine that the device is positioned incorrectly and output a warning to, for example, a console or other output device (not shown), such as a speaker, display, or other output associated with the MCS device 101.

Figure 6:
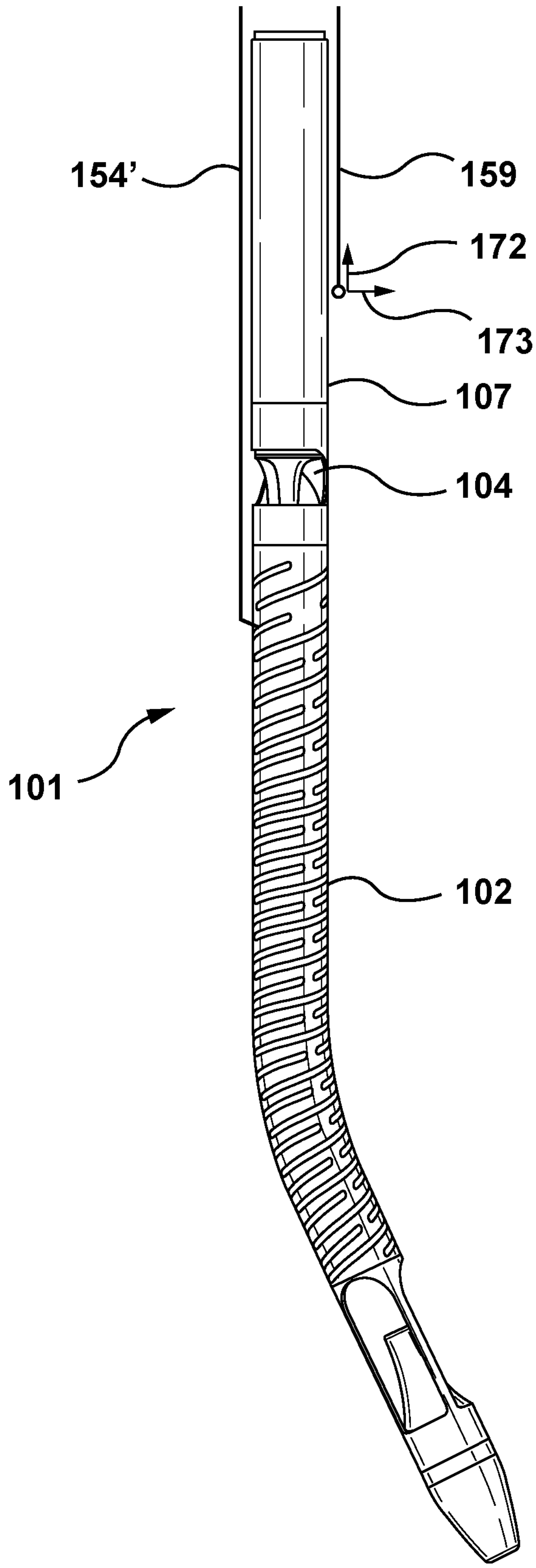
FIG. 6 is a side view of an example MCS device having a first fiber optic positioned to measure flow through an inlet tube and a second fiber optic positioned to measure flow around the device, where the second fiber optic is adapted to measure at least two velocity components.
Figure 7:
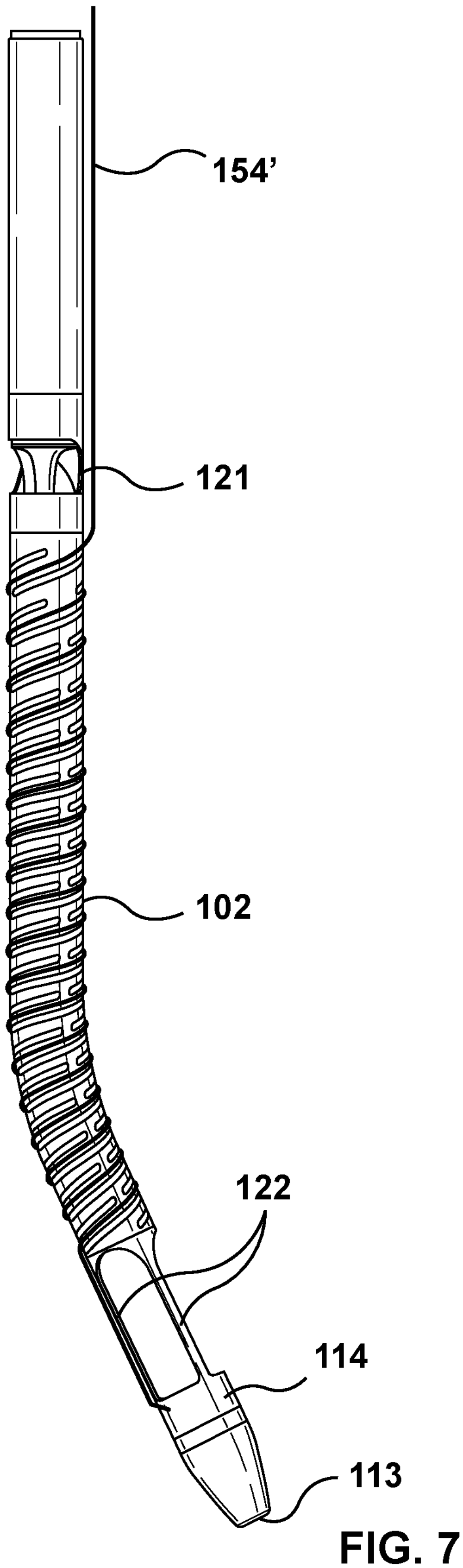
FIG. 7 is a side view of an example MCS device showing how one or more optical fibers may be connected to the MCS device and coiled around an inlet tube following a pitch of laser cuts in a structural component of the inlet tube.

Optionally, as shown schematically in FIG. 6, LDV measurement outside the inlet cannula 102 and proximal to the outlet windows 104 may include measuring at least two velocity components: a linear velocity component 172 and a rotational velocity component 173. The linear velocity component 172 may be considered to be parallel to a central axis of the MCS device 101 or housing of the motor 107, or alternatively parallel to a central axis of the vessel (e.g., aorta) in which the measurement is taken. The rotational velocity component 173 may be considered to be tangential to a circumference of the MCS device 101 or housing of the motor 107. Because the blood flow proximal to the outlet windows 104 during operation of the pump in a beating heart may contain a large rotational component as well as linear component, measuring both components may allow a more accurate measurement of true blood flow. Optionally, a controller may calculate total blood flow summing these two components or summing factors of each component. Optionally, a controller may monitor a ratio of the linear velocity component 172 and rotational velocity component 173, which may be an indication of a ratio of natural blood flow 125 vs pumped blood flow 120. An algorithm may monitor the ratio over time, which may be an indication of the patient's or device's status. Optionally, the two-component LDV measurement may be taken by splitting a laser emitted from one fiber using a prism (not shown) that directs two beams at a known angle to one another, up to and preferably 90 degrees. For example, a first beam may be directed along a plane that is parallel to an axis of the MCS device 101 and a second beam along a plane transverse to the axis of the MCS device 101.

Optionally, a calculated velocity or volumetric flowrate may be used as a feedback parameter in the control of the MCS device's impeller speed. Additionally or alternatively, a calculated velocity or volumetric flowrate may be used as a feedback parameter in control of another flow device type (such as in a non-medical application) using an LDV system. In some embodiments, a control console may have an impeller speed control algorithm stored on an electronic storage medium contained within or in communication with the controller. The controller may be configured to, as part of an impeller speed control algorithm, accept a user selected input for a desired set flowrate and output a motor voltage or control signal associated with a motor voltage to operate the motor that drives the impeller at an initial setpoint. A resulting blood flowrate through the MCS or other device, or optionally, around or both through and around the MCS or other device, may be detected and calculated, for example, using calculation and data processing techniques described herein. The controller may compare the calculated flowrate with the desired set flowrate and adjust the output motor voltage accordingly to bring the calculated flowrate toward the set flowrate.

Optionally, a calculated velocity or volumetric flowrate may be used as a feedback parameter in a control algorithm to assess functionality of the MCS device or another flow device type (such as in a non-medical application) using an LDV system. For example, experiential data may be collected to determine a range of flowrate of blood through a properly functioning MCS device that may be associated with a given motor current draw or motor voltage output (or vice versa). If, in use, the calculated velocity or flowrate is not within an expected range for the motor current draw or motor voltage, the controller may determine that the MCS device is not functioning as expected and output a signal to cause an action to occur. For example, the controller may cause a warning message to be displayed, adjust an operating setpoint, or cause to perform another action. For example, if calculated velocity or flowrate is lower than the expected range for a given motor current draw or voltage, the MCS device may have an occluded inlet window. If the controller determines that the velocity or flowrate is below an expected range, the controller may output a warning signal to cause a warning message to a user that a possible occlusion or suction event may be occurring and to remedy by adjusting position of the MCS device, Additionally or alternatively, the controller, through a suction event remedy algorithm, may be performed wherein the motor is controlled to pause or reverse for a brief period (e.g., less than or equal to 2 seconds, less than or equal to 1 second) then return to the previous speed, optionally ramping up to the previous speed.

FIG. 7 shows an example embodiment wherein one or more optical fibers are connected to a MCS device 101 and coiled around an inlet tube 102, for example, following a pitch of laser cuts in a structural component of the inlet tube. Distal tips of the optical fiber(s) may terminate somewhere along a length of the inlet tube to measure flow rate 118 in the inlet tube 102. Alternatively, as shown in FIG. 7, one or more optical fibers may terminate distal to the inlet tube, for example, in a nose piece 114 aiming forward (for example, forward may be where the one or more optical fibers may be aimed distal to the nose piece to measure flow in front of the tip of the catheter) or aiming backward (for example, backward may be where the one or more optical fibers may be aimed into the inlet tube from the nose piece 114, which may include a micro-optic prism (not shown) or lens (not shown) to direct an emitted beam or reflected light). Such an arrangement may have an advantage of less interruption of flow in the inlet tube 102 or ease of manufacturing.

Figure 8:
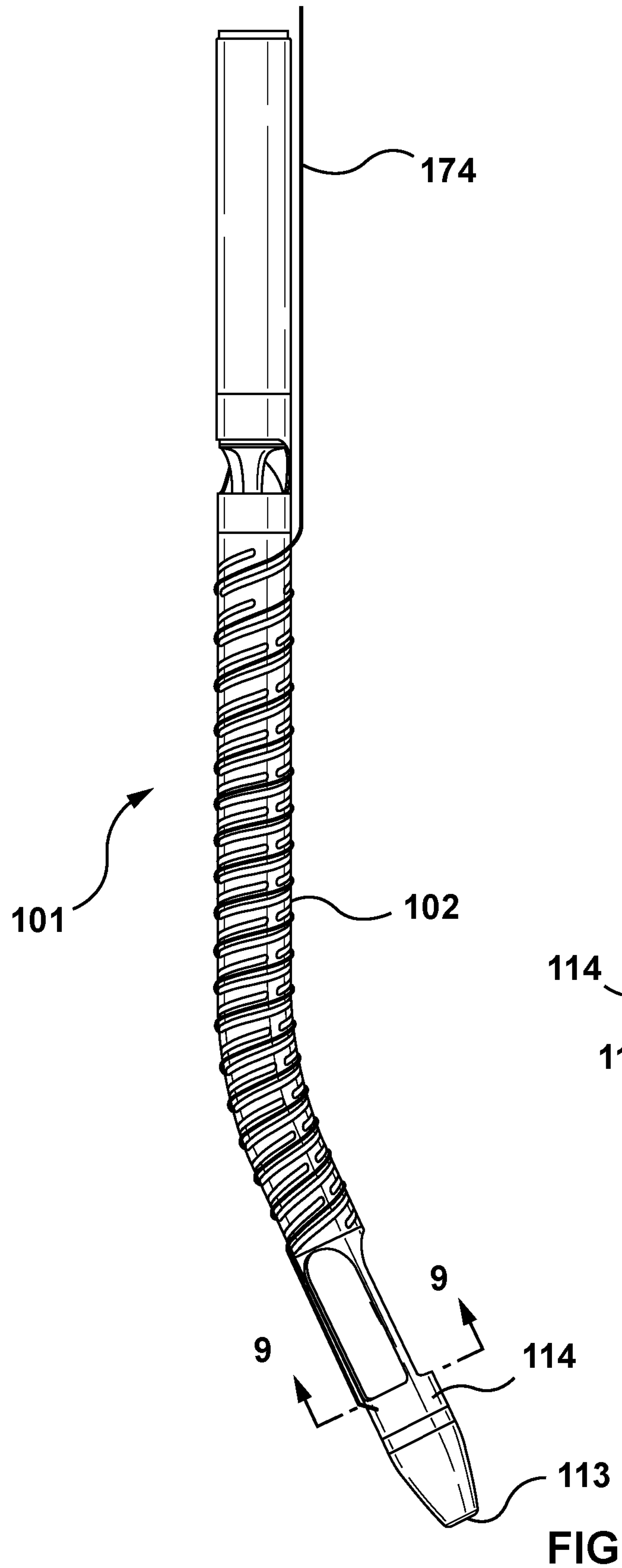
FIGS. 8 and 9 are side and cross-sectional views, respectively, of an example MCS device adapted to emit a laser from a distal end into an inlet tube of the device.
Figure 9:
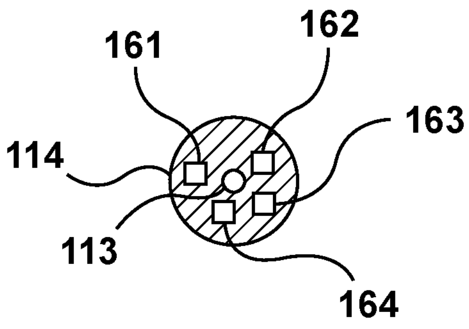

FIG. 8 shows an alternative embodiment of an MCS device 101 having a laser source and receptor contained in a nose piece 114. FIG. 9 shows a schematic cross section of the device of FIG. 8 as taken along the line 9-9 indicated in FIG. 8. The embodiment of FIG. 8 does not use optical fibers to transmit light along a length of the catheter from the laser source to the inlet tube or region proximate to the MCS device. In the embodiment of FIG. 8, a laser source 161, such as a Vertical-Cavity Surface-Emitting Laser (VCSEL) and one or more photodiodes 162, 163 may be integrated into the nosepiece 114, optionally allowing space for a guidewire lumen 113. Additional electronics, such as a preamplifier, driver or analog/digital converter 164 may be contained within the nosepiece 114. Optionally, an electronics manifold or circuit board that connects the laser source 161, photodiode(s) 162, 163 and additional electronics 164 to one another and to a conductor 174 may be included in the nosepiece 114. The conductor 174 may transmit a signal, such as a digital signal, from the electronics in the nosepiece 114 to a control console external to the patient where the signal is processed to provide assessment of blood flow rate. Furthermore, the conductor 174 may also send electrical power from the console to the laser source and additional electronics. The conductor 174 may be helically wound around the inlet tube 102, optionally following helical laser cuts (e.g., between or within laser cuts) in the inlet tube, and fastened to the inlet tube, for example, with adhesive or held in place between a membrane 124 (not shown) and the nose piece 114. Helical winding of the conductor 174 may allow the inlet tube 102 to remain flexible.

In one or more of the configurations disclosed, light absorption by blood in a patient may be measured, optionally over a range of frequencies and/or optionally in moving or still blood, to assess hemoglobin concentration. Blood has different absorption spectra for different oxygenation levels. A software algorithm stored in a control console 150 may use input such as delivered light intensity and frequency and/or intensity of light captured by a photodiode 152 to calculate light absorption, which may be used in a lookup table to identify hemoglobin concentration of the blood.

In one or more of the configurations disclosed, laser light scattering by a patient's blood may be measured over a range of wavelengths to assess hemoglobin concentration. Wavelength of light is an important parameter in determining non-trivial absorption and the scattering-spectrum of blood. The scattering-spectrum of blood also depends on oxy-hemoglobin content. Oxy-hemoglobin content of blood may be calculated by evaluation of an absorption spectrum or amplitude of reflected light. A tunable laser light source may be advantageous to obtain such a spectrum. Optionally, the LDV module 156 or control console 150 may be configured to allow a user to tune the laser light source wavelength, for example, within a range of 390 to 750 nm (optionally in a range of 640 to 750 nm). In some embodiments, a user-controlled actuator may adjust the wavelength of the laser light source or may signal an algorithm to deliver a range of wavelengths to obtain a resulting absorption spectrum, which may be used to evaluate oxy-hemoglobin content of the blood. The controller 150 may display oxy-hemoglobin content on a user interface.

Example Evaluation of LDV Measurements.

In any of the configurations disclosed herein, fluid parameters may be determined or assessed based on LDV measurements. For example, viscosity of the blood flowing through the inlet cannula 102 may be assessed from the shape of Doppler spectra captured by the photodiode as a result of passing light from an optical fiber through the blood flow. Similarly, viscosity of fluid flowing through a pipe or cannula may be assessed by the shape of Doppler spectra captured by a photodiode as a result of passing light from an optical fiber through fluid flow.

Viscosity may be conceptualized as quantifying the internal frictional force that arises between adjacent layers of fluid that are in relative motion. For example, when a fluid is forced through a tube, the fluid flows more quickly near the tube's axis than near its walls. Viscosity is related to and may be proportional to, the difference in flow rate near an axis and the flow rate near a wall. Light from a laser focused on a particular region in the inlet cannula, for example, a high flow region near or at the axis of the inlet cannula, may be reflected off of blood in the beam path, including slower moving blood near the wall, faster moving blood near the axis, and blood flowing in a range between the slower and faster moving blood. Thus, a broad scattering of light may indicate different velocity components, which may in turn lead to a broad Doppler spectrum. The shape of the Doppler spectrum may be an indicator of the viscosity of the medium since higher viscosity media exhibit more velocity components (towards the edge of the tube) as compared to lower viscosity media.

A Doppler parameter may be understood here to mean a parameter representing a change in a frequency of a signal output from a fluid from a frequency of a signal input to the fluid. In some examples, the Doppler parameter may correspond to a Doppler shift. A Doppler spectrum may be understood to mean a spectrum which includes frequencies of a signal output from a fluid and frequencies of a signal input to the fluid. Thus, it is possible to evaluate the Doppler shift of different frequency components of signals output from a fluid relative to the different frequency components of signals input to the fluid. The range of frequencies may be represented by a width of the Doppler spectrum. A larger range in blood flow may result in a larger range of frequencies from light received in the fluid and may, therefore, provide an evaluation of viscosity.

Figure 10:
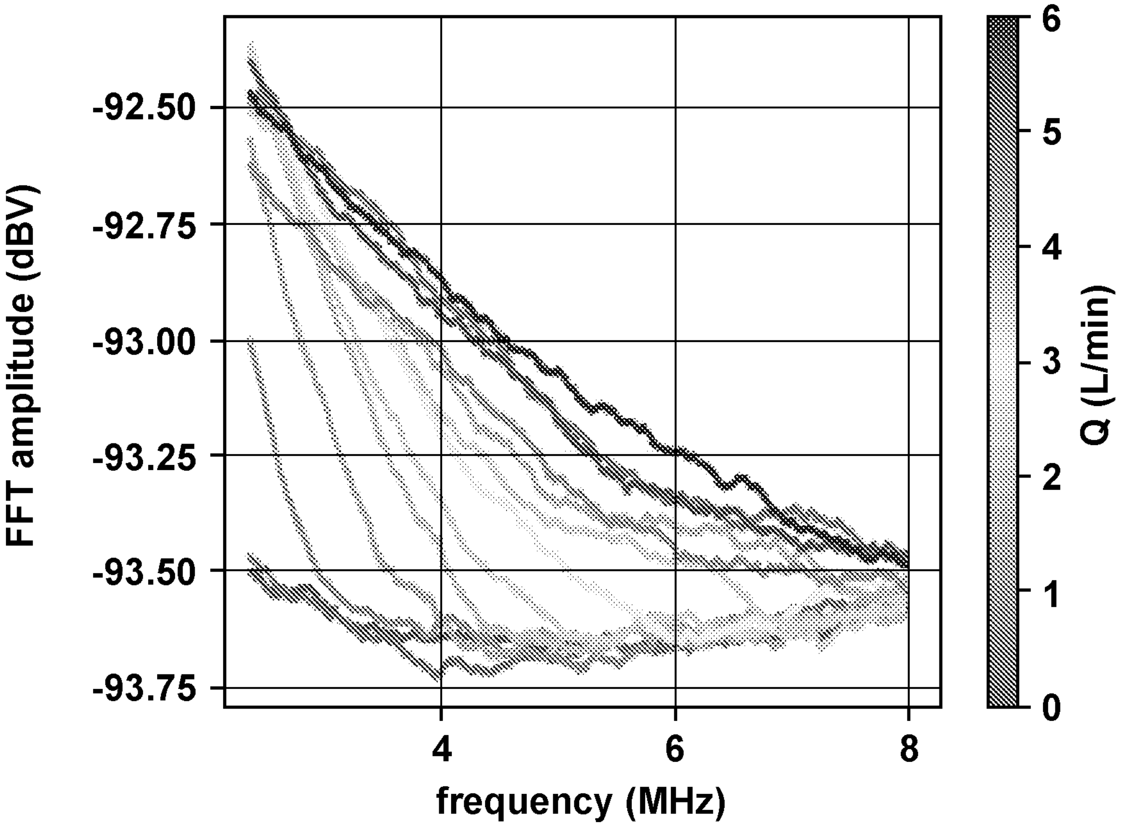
FIG. 10 is a plot of example experimental results of a laser doppler apparatus assessing blood flow, showing Fast Fourier transform (FFT) amplitudes versus frequency resulting from different time series measurements of backscattered light at externally applied volume flows (Q).
Figure 11:
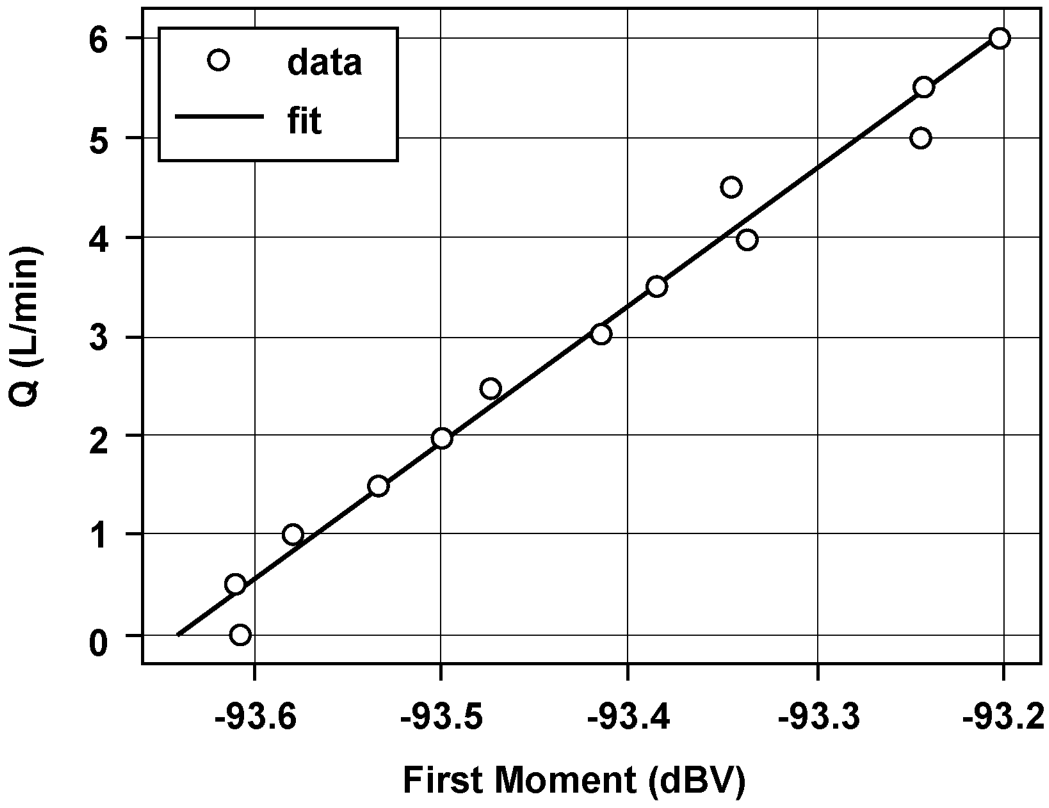
FIG. 11 is a plot of example experimental results of a laser doppler apparatus assessing blood flow, where a relationship between first moment and flow rate is determined.

Evaluation of volumetric flow rate using LDV may be performed based on the first weighted moment of the power density spectrum of the Doppler shifted optical signal (e.g., the mean shift frequency). For example, FIG. 10 shows a plot of power density spectra for different flow rates Q between 0 L/min and 6 L/min. FIG. 11 shows the first weighted moment of the power density spectrum of FIG. 10 for different flow rates Q between 0 L/min and 6 L/min. The relationship of flow rate and first weighted moment has been proposed to be a linear relationship, for example by R. F. Bonner and R. Nossal, MODEL FOR LASER DOPPLER MEASUREMENTS OF BLOOD FLOW IN TISSUE, Appl. Opt. 20, No. 12, (1981), pp. 2097-2107, the entire content of which is incorporated by reference herein for all purposes and forms a part of this specification. This linear dependence may allow for a determination of the flow rate with a simple normalization.

Advanced procedures for accurate evaluation of volumetric flowrate of fluid flowing through a tube, such as blood flowing through a MCS device, are disclosed herein to 1) reduce spectral noise background and/or 2) account for a non-linear relationship between observed flow rates and first weighted moment of resulting power density spectra. A non-linear relationship may be caused by flow disturbance in the inlet cannula or in the vicinity of the fiber end.

An optical measurement head, for example the distal terminating tip of the optical fiber 165, also referred to as a fiber facet, may cause perturbations in the flow of fluid contacting it. A Doppler spectra may vary and may be prone to noise, especially at higher frequencies, due to such perturbations and their effect on light penetration depth. Large signal strengths at higher frequencies may be beneficial. Flow information of the fastest particles, generally present in the undisturbed flow regions (i.e. near the axis), is associated with higher frequencies. Different tube geometries and/or different optical measurement head positions may also influence Doppler spectra. To improve accuracy, in some embodiments spectral noise may be reduced by incorporating into the systems disclosed herein one, some or all of the following features, including: a) superimposing a flow disturbance, b) using light with a wavelength greater than 634 nm (e.g., greater than or equal to 670 nm), and/or c) using a computer to process data numerically.

Superimposing a flow disturbance may be achieved by including one or more objects into the flow path, relative to the measurement head 3. The one or more objects may disturb the flow through the inlet cannula 102 upstream of the measurement head 3 (e.g., distal termination of the optical fiber). The one or more objects may be a protrusion from a side wall of the inlet tube into the flow lumen having a geometry and distance from the measurement head 3 sufficient to cause a flow disturbance that will reach the measurement head 3. In some embodiments, the one or more objects may be in the form of a pin or pillar having a width or diameter in a range of 0.2 mm to 1 mm, or of a width or diameter greater than or less than that range and a height capable of causing a disturbance to reach the measurement head 3 under typical operating conditions (e.g., in a range of 0.1 to 1 mm, or of a value greater than or less than that range). In some embodiments, the one or more objects may be a groove or ridge having a depth or height in a range of 0.5 mm to 1 mm, or of a value greater than or less than that range, and an angle to flow direction in a range of 15 degrees to 90 degrees, or of a value greater than or less than that range. In some embodiments, the one or more objects may be positioned at a distance between 0 and 20 cm (e.g., optionally in a range of 5 mm to 30 mm, or of a value greater than or less than that range) upstream of the measurement head 3, for example in the inlet cannula 102 or in an inlet window 103. The one or more objects may create a flow disturbance superimposed onto the flow disturbance caused by the measurement head 3 so that a greater number of faster particles may be captured and the measurement result may be more accurate.

In some embodiments, for measurement of turbid media such as blood, a laser wavelength having an effective penetration depth greater than 0.6 mm may be chosen to reduce noise and improve accuracy. The effective penetration depth is equal to 1/effective attenuation coefficient. In some embodiments, for measurement of blood, a wavelength greater than 634 nm may penetrate deeper than 0.6 mm and may optionally be used in the systems disclosed herein.

In some embodiments, accuracy of the determination of flowrate in a MCS device 101 using LDV may be improved by using a first data processing procedure (e.g., operated by a processor or FPGA) during manufacturing of the MCS device to determine background noise and an accurate relationship between velocity and first weighted moment of a frequency spectrum v(fm). The first data processing procedure may be digitally stored on the MCS device 101 (e.g., in an electronic storage medium such as an EPROM) and read by a controller during use in a patient for a second data processing procedure to calculate flowrate of blood through the MCS device. The stored accurate relationship between first weighted moment and velocity or flowrate may be, for example, in the form of a formula or lookup table. Volumetric flowrate may be determined from velocity when a cross-sectional area or volume of the inlet tube 102 is known. A similar procedure may be used to apply to other devices using LDV during manufacture of the device.

Figure 12:
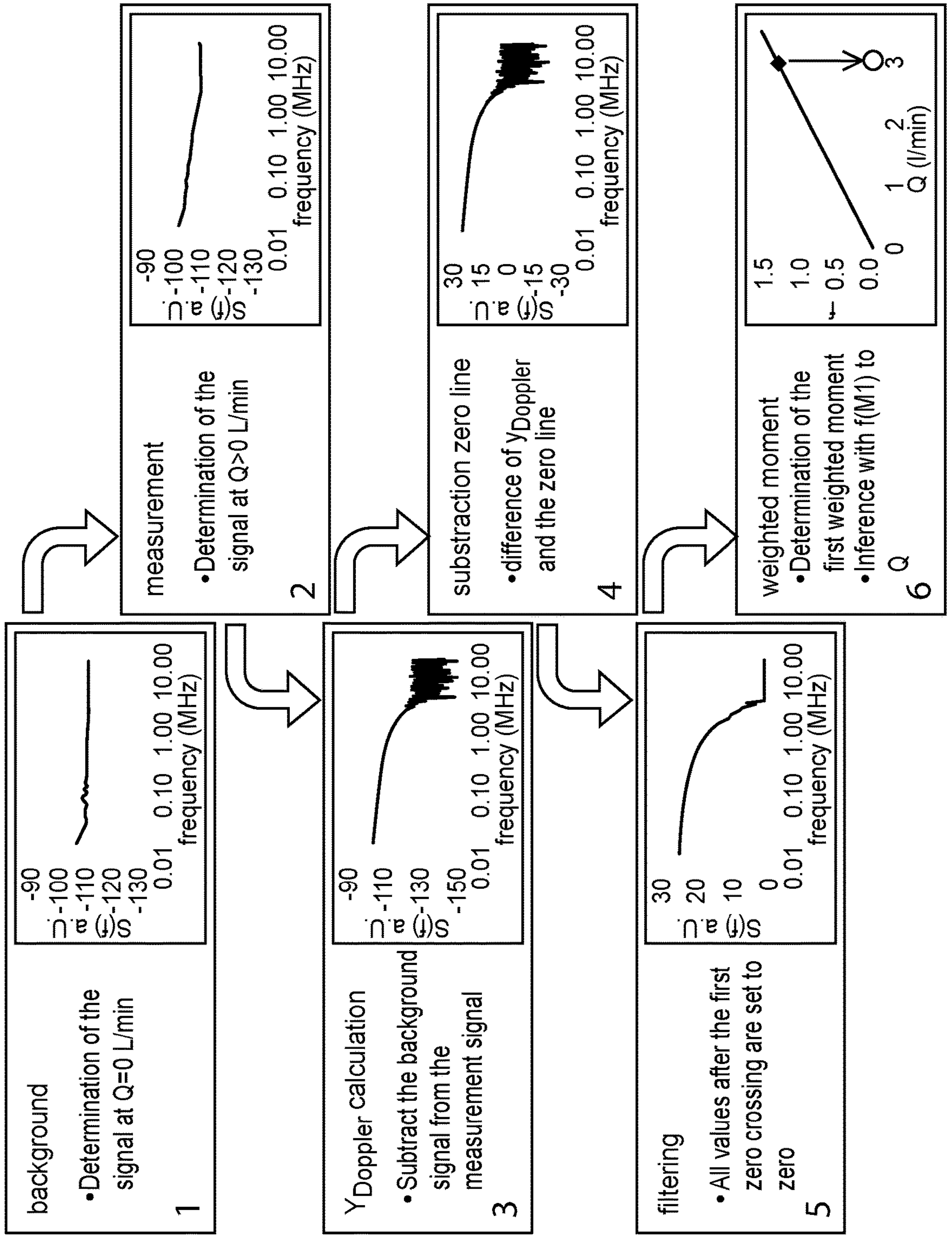
FIG. 12 is a diagram of an example data process scheme for reducing background spectral noise to improve accuracy of flow measurement.

When in use in an MCS device in a patient, spectral data may be obtained by delivering light to blood in the inlet cannula, for example, with a system disclosed herein, and flowrate may be determined by involving the second data processing procedure, wherein the controller of the computerized console 150 may read a stored background noise signal and accurate relationship from the storage medium in the MCS device and a first weighted moment of the spectral data may be calculated by a processor in the controller using data processing steps that filter out the background noise signal, and flowrate may be determined by inputting the first weighted moment into the accurate relationship. The first data processing procedure performed during manufacturing may include steps 1 to 6 of the following scheme as illustrated by FIG. 12:

1. In a first step, one or more hardware processors may measure and store a background spectrum $s_{bg}(f)$, for example, by generating a spectrum in still blood (flowrate Q=0 L/min), or in a similar medium having similar particles and scattering patterns, or in air. This step may be done prior to use of the MCS device in a patient. For example, the background spectrum may be measured in a laboratory setting or during a manufacturing process. The process may be done with an MCS device model and applied to each MCS device of said model. The process may be done with a sample of a batch of manufactured MCS devices and applied to each MCS device in the batch. Additionally or alternatively, the process may be done with each MCS device and applied to each specific MCS device. In some embodiments, this step may be performed by a test apparatus having a testing processor. Optionally, the background spectrum may be stored in an electronic medium associated with each MCS device to which the spectrum is to be applied, for example on an EPROM in the MCS device.
2. In a second step, one or more hardware processors may measure a photodiode signal, and calculate and store a frequency spectrum s(f) with the measurement head (distal terminating tip of the optical fiber 165) in blood, or a similar medium, flowing in a range of interest, such as between 0 L/min and 6 L/min. This step may be done by a test apparatus having a testing processor in a laboratory setting before using the MCS device in a patient. The photodiode signal measurement and the frequency spectrum calculation and storage may be performed by one or more processors in the test apparatus. The frequency spectrum may be stored in an electronic medium in the testing apparatus.

Figure 13:
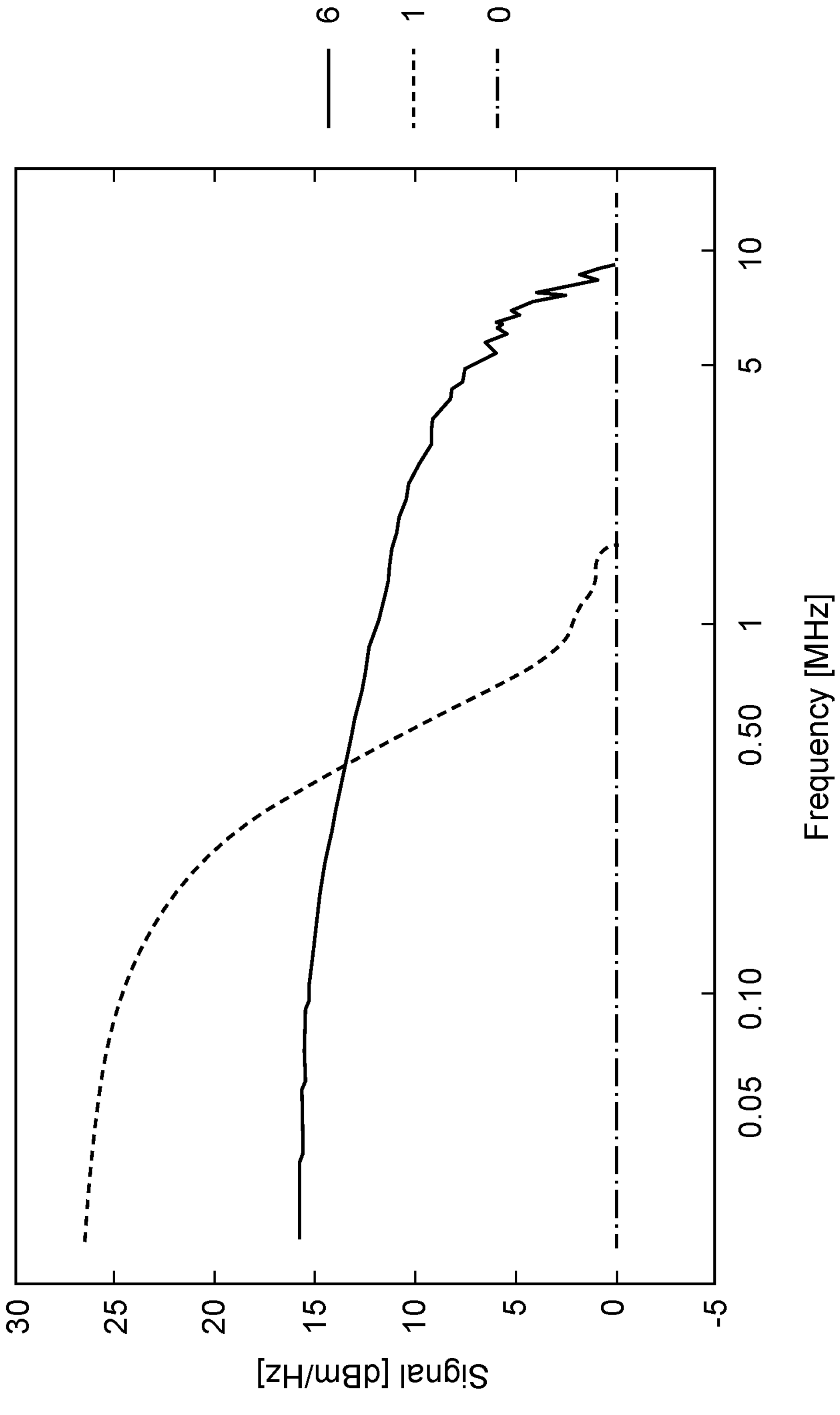
FIG. 13 shows an outcome of an example filtering step in a noise reduction data processing scheme.
Figure 14:
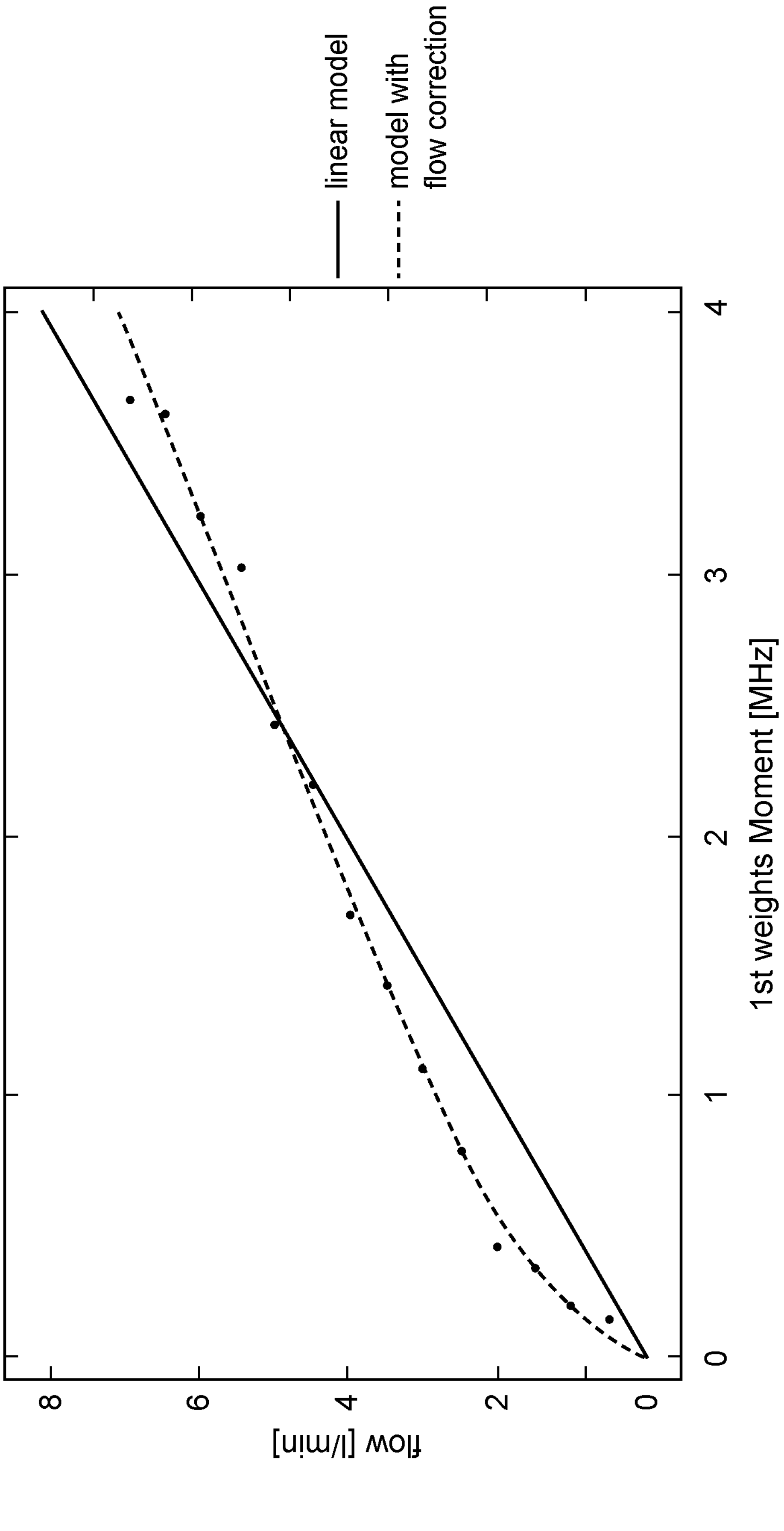
FIG. 14 shows a linear relationship and a more accurate non-linear relationship between first weighted moment of a power density spectra and flowrate.

3. In a third step, one or more hardware processors may calculate a background-corrected Doppler spectrum $s_{Doppler}(f)$. The one or more hardware processors may calculate the background-corrected Doppler spectrum $s_{Doppler}(f)$ by subtracting a background signal $s_{bg}(f)$ from a measurement signal s(f). This step may be done by a test apparatus having a testing processor in a laboratory setting before using the MCS device in a patient and the corrected Doppler spectrum may be stored in an electronic medium in the testing apparatus.
4. In a fourth step, one or more hardware processors may subtract the baseline by subtracting the average or median of the corrected Doppler spectrum data $s_{Doppler}(f)$, for $f>f_{max}$, where $f_{max}=2*v_{max}/\lambda_0$, where $v_{max}$ is the highest expected flow velocity and $\lambda_0$ is the laser wavelength. This step may be done by a test apparatus having a testing processor in a laboratory setting before using the MCS device in a patient and the result may be stored in an electronic medium in the testing apparatus. For example, for $\lambda_0$ above 640 nm, a known diameter of the tube (e.g. 6 mm) 1 and a flow rate of Q=6 L/min, the highest expected flow velocity $v_{max}$=3.8 m/s.
5. In a fifth step, the one or more hardware processors may smooth data from step 4 by averaging or applying a low pass filter and discarding frequency spectra data which are below zero or whose frequency are above $f_{max}$. FIG. 13 shows an outcome of this process, showing data for flowrates of 0, 1 and 6 L/min. Optionally, data may be gathered using other flowrates within an applicable range, for example for flowrates of 1, 2, 3, 4, 5, and 6 L/min when the applicable range is 0 to 61/min. This step may be done by a test apparatus having a testing processor in a laboratory setting before using the MCS device in a patient and the result may be stored in an electronic medium in the testing apparatus.
6. In a sixth step, the one or more hardware processors may calculate the first weighted moment from the filtered and smoothed spectral data for known flow rates from step 5 and generate a relationship between velocity or volumetric flowrate as a function of first moment v(fm), which may be a linear relationship, such as shown in FIG. 11, or a non-linear relationship, such as shown in FIG. 14, which may be determined using methods disclosed herein. The relationship v(fm) may be stored on the tested MCS device, and optionally, other MCS devices related to the tested device, for example devices of the same manufacturing batch.

The second data processing procedure, performed by the control console 150 during use of the MCS device 101 in a patient, may include the following scheme, in which steps 2 to 5 replicate steps 2 to 5 of the first data processing procedure to filter out background noise and generate a first weighted moment, which may be input into the relationship v(fm) determined in the first data processing procedure to determine flowrate:

1. In a first step, one or more hardware processors (e.g. of the control console 150), may be configured to read the background spectrum $s_{bg}(f)$ from storage medium of the MCS device 101.
2. In a second step, one or more hardware processors (e.g. of the control console 150), may be configured to deliver light from the LDV module 156 to the MCS device 101, measure a photodiode signal, and calculate and store a frequency spectrum s(f) with the measurement head (distal terminating tip of the optical fiber 165) in blood.
3. In a third step, one or more hardware processors (e.g. of the control console 150), may be configured to calculate the background-corrected Doppler spectrum $s_{Doppler}(f)$ by subtracting the background signal $s_{bg}(f)$ from the measurement signal s(f).
4. In a fourth step, one or more hardware processors (e.g. of the control console 150), may be configured to subtract the baseline by subtracting the average or median of the corrected Doppler spectrum data $s_{Doppler}(f)$, for $f>f_{max}$, where $f_{max}=2*v_{max}/\lambda_0$, where $v_{max}$ is the highest expected flow velocity and is the laser wavelength.
5. In a fifth step, one or more hardware processors (e.g. of the control console 150), may be configured to smooth the data from step 4 by averaging or applying a low pass filter and discarding frequency spectra data which are below zero or whose frequency are above $f_{max}$.
6. In a sixth step, one or more hardware processors (e.g. of the control console 150), may be configured to calculate first weighted moment of the data from step 5 and determine flowrate from the relationship first weighted moment v(fm) stored on the MCS device from the first data processing procedure.

By reducing spectral noise with these features and techniques, the deviations between repeated measurements may be reduced by a factor of, for example, 6.

Accuracy of flow rate measurement may be additionally or alternatively improved by accounting for a non-linear relationship between observed flow rates in the MCS device and first weighted moment of resulting power density spectra. This may be done prior to use of the MCS device in a patient. In some embodiments, the non-linear relationship may be determined in a laboratory setting. In some embodiments, the non-linear relationship may be determined during a manufacturing process. In some embodiments, the non-linear relationship may be determined with a model device, a batch of devices, or each device. In some embodiments, the non-linear relationship may be determined with an MCS device model and applied to each MCS device of said model. In some embodiments, the non-linear relationship may be determined with a sample of a batch of manufactured MCS devices and applied to each MCS device in the batch. In some embodiments, the non-linear relationship may be determined for each MCS device and applied to each specific MCS device. By determining a non-linear relationship for a batch or MCS devices or for each specific MCS device, differences in each batch or device that may affect flow properties (for example, due to tolerance of dimensions or positioning of the optical fiber) may be accounted for. Optionally, the non-linear relationship may be stored in an electronic medium associated with each MCS device to which the relationship is to be applied, for example on an EPROM in the MCS device. In some embodiments, when a MCS device 101 is connected to a control console 150, the non-linear relationship may be read by the control console for use in determining flow rate from first weighted moment of a power density spectra. In some embodiments, the non-linear relationship may be stored in a form of an equation (e.g., a high order polynomial equation), extrapolation between data points, a lookup table, or a characteristic map.

Figure 15:
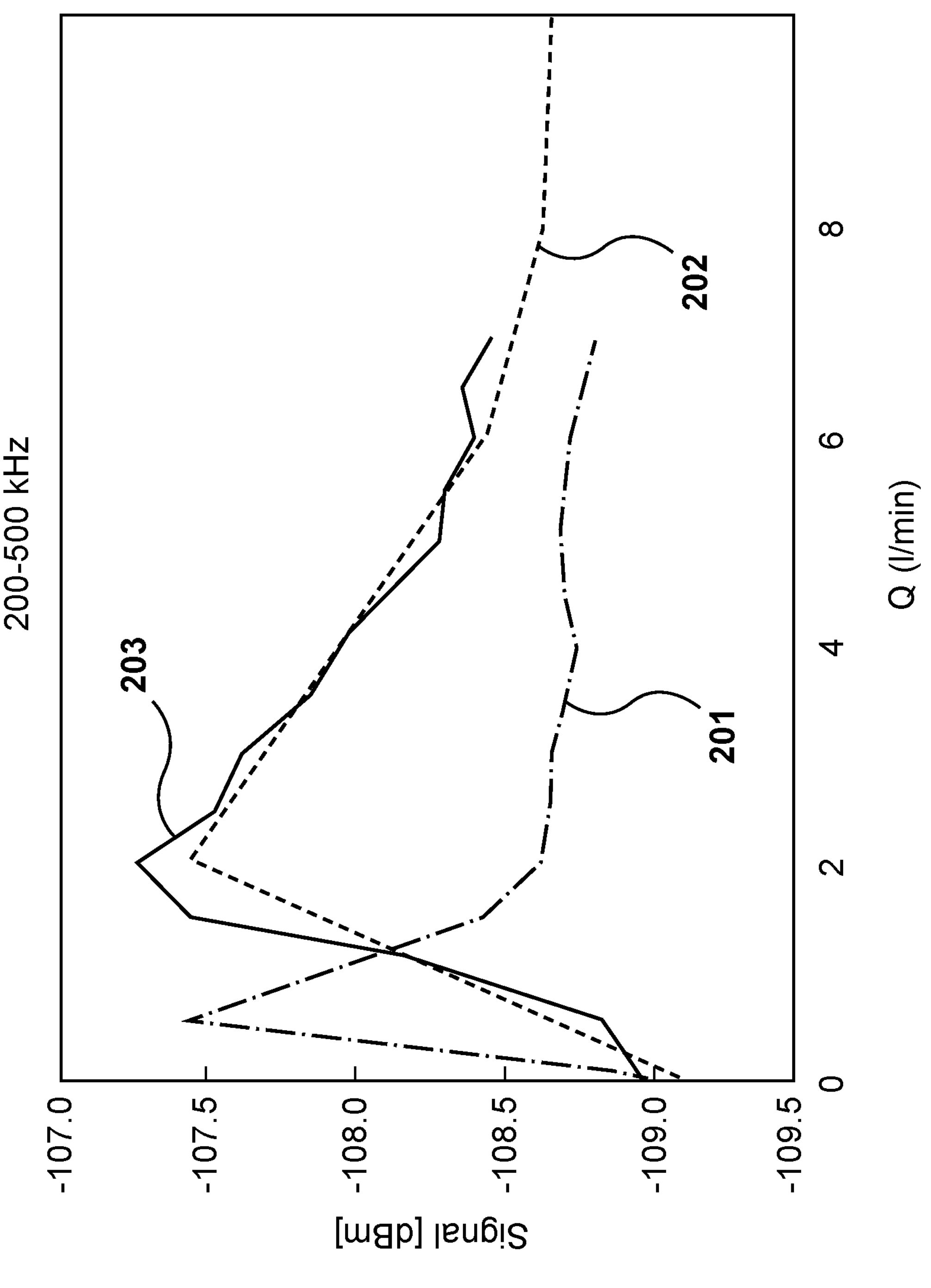
FIG. 15 is an example bin representation plot of the 200-500 kHz range mean power density versus flowrates through an example MCS inlet cannula for different lengths of the cannula.
Figure 16:
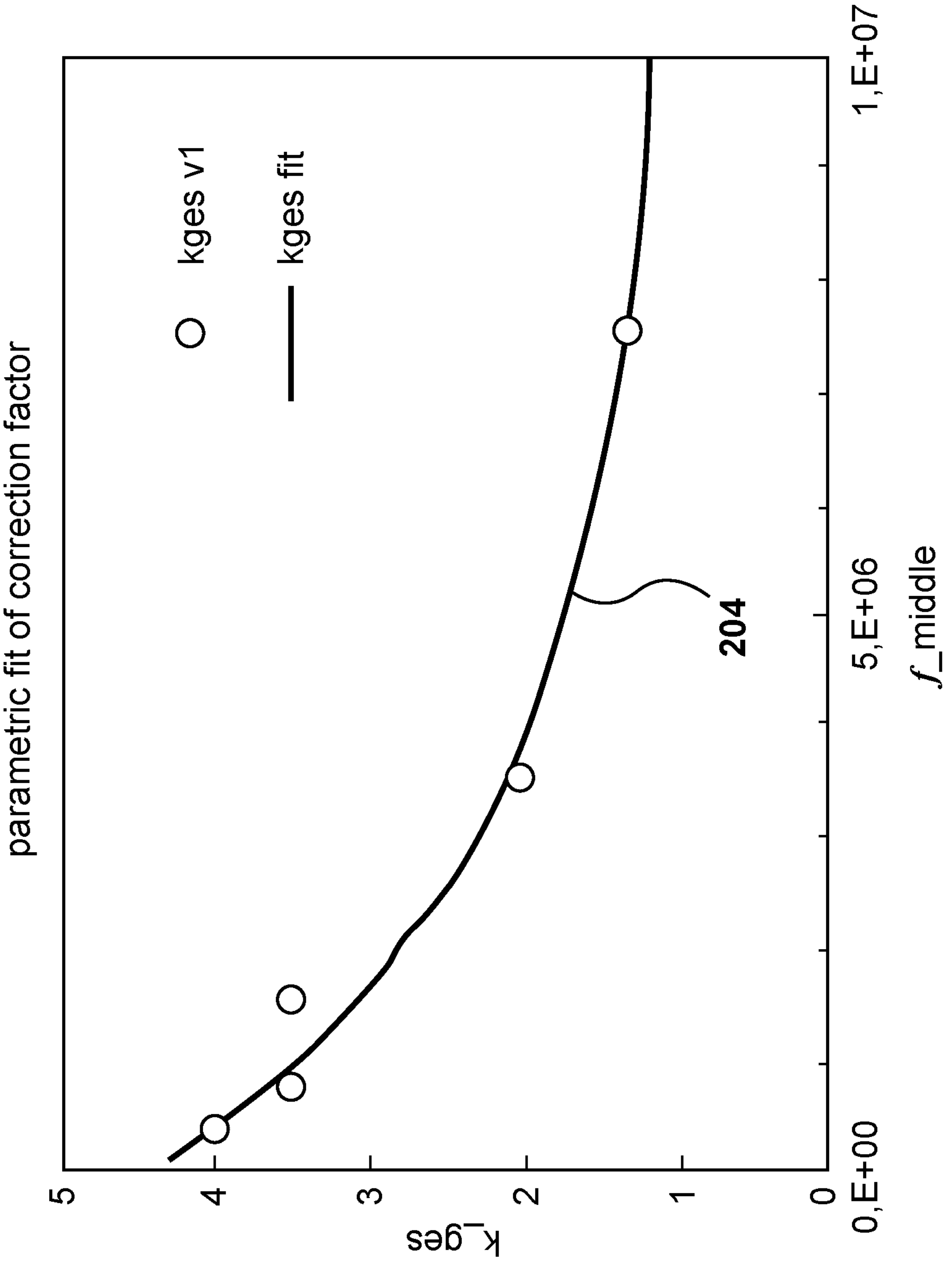
FIG. 16 is an example plot of a calibration factor, $k_{ges}$, in dependence of frequency bin, showing a line of parametric fit.

A processor or FPGA may perform a numerical correction algorithm stored on a medium to treat data to determine a non-linear relationship between first moment and flowrate that is more accurate than a linear relationship. For example, a more accurate non-linear relationship between first weighted moment of a frequency spectra and flowrate may be determined by calculating a factor, $k_{ges}$ by: (1) measuring and storing a power density spectra for different flowrates through the MCS inlet cannula (see FIG. 10) and dividing it into suitable frequency bins (see FIG. 15); (2) comparing the frequency bins to those of a known reference dataset; (3) calculating the factor, $k_{ges}$, that transforms the tested dataset to approximate the reference dataset. In the example in FIG. 15, a flow rate (Q) of a tested device's original dataset 201 is stretched to the test device's new data set 202 with a factor $k_{ges}$ to approximate a reference dataset 203. This accounts for the linearity transformation between the geometry of a tested MCS device to a reference geometry. For example, a reference geometry may be a standard MCS device or pipe apparatus having an accurately known flowrate to first moment relationship predetermined in a lab. Each batch sample or specific MCS device may be assessed in comparison to the reference dataset to calculate the factor $k_{ges}$ that is appropriate for that batch sample or specific MCS device. The needed factor decreases with increasing frequency, as shown in FIG. 16, a plot of calibration factor, $k_{ges}$, in dependence of frequency bin, showing a $k_{ges}$ line of parametric fit 204, which may be described by the function $k_{ges}=1+k1*e^{-k2*fm}$, where fm is the middle frequency of the used frequency range, and k1 and k2 are fitting parameters. In the example shown in FIG. 16, k1=3.4 and $k2=3.3*10^{-7}$ $Hz^{-1}$.

A non-linear relationship between first weighted moment of a frequency power density spectra and flow rate may be determined by a function, wherein $Q=(k0/k_{ges})*f_m$, where k0 is the linear proportionality factor between $f_m$ and Q, and $k_{ges}=1+k1*e^{-k2*fm}$ and accounts for the nonlinearity correction. FIG. 14 shows example results of the process, wherein a more accurate non-linear relationship is compared to a linear relationship, to obtain the example non-linear relationship, which improved accuracy of flow measurement for the tested MCS device by a factor of 2.

The resulting non-linear relationship between first weighted moment of a frequency power density spectra and flowrate may optionally be stored on a memory medium such as an EPROM in each MCS device associated with the defined relationship. The non-linear relationship may be read and used by a computerized algorithm in the control console to determine flow rate during use of the MCS device in a patient. Optionally, this non-linear relationship may be used in combination with a background spectral noise reduction process such as the process described above.

Terminology

While the above techniques may be applied in a medical context, techniques for determining flow velocity may be applied in a non-medical context as well. While in some examples, a fluid being measured is referred to as blood having blood cells, other fluid flow may be measured. For example, flow of a fluid having particulates capable of scattering light may be measured. In some examples, while the body of a patient may be referred to herein, the same techniques may be applied to any container of fluid. While the techniques herein are sometimes described with reference to an MCS device, some techniques described herein may be applied to work with or without an MCS device or with a pumping or pumping support system for fluid measured by an LDV system.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A mechanical circulatory support (MCS) device configured to at least partially implant in a heart of a patient, the MCS device comprising:
- an inlet portion;
- an outflow portion;
- a catheter;
- a proximal hub;
- a connector configured to connect the catheter to a control console; and
- an optical fiber extending from a proximal ex vivo region to a distal in vivo region, wherein a distal terminating tip of the optical fiber is positioned in the inlet portion of the MCS device.

2. The MCS device of claim 1, wherein the inlet portion comprises an inlet cannula.

3. The MCS device of claim 1, further comprising a micro-optic lens connected to the distal terminating tip.

4. The MCS device of claim 1, wherein at least a portion of the optical fiber is positioned between a structural layer and a membrane of the inlet portion.

5. The MCS device of claim 1, further comprising a second optical fiber having a measurement head or distal terminating tip positioned exterior to the MCS device.

6. The MCS device of claim 1, wherein at least a portion of the optical fiber is positioned on an exterior surface of a structural layer of the inlet portion in a helical configuration.

7. The MCS device of claim 6, wherein the helical configuration is aligned with a helical configuration of laser cuts in the structural layer.

8. The MCS device of claim 1, further comprising a nose piece and wherein the distal terminating tip of the optical fiber is positioned at least in part within the nose piece.

9. A system for determining volumetric flowrate of fluid through a mechanical circulatory support (MCS) device using Laser Doppler Velocimetry (LDV), the system comprising:
- the MCS device, the MCS device comprising:
  - an inlet portion;
  - an outflow portion;
  - a catheter;
  - a proximal hub;
  - a connector configured to connect the catheter to a control console; and
  - an optical fiber extending from a proximal ex vivo region to a distal in vivo region, wherein a distal terminating tip of the optical fiber is positioned in the inlet portion of the MCS device;
- a photodiode configured to generate a signal associated with light attenuated by fluid flowing through the MCS device; and
- one or more hardware processors in communication with the photodiode and configured to execute a computer operable algorithm for reducing spectral noise in the signal.

10. The system of claim 9, wherein the optical fiber is configured to transmit light to, or receive light from, moving fluid particles in the inlet portion of the MCS device, wherein the distal terminating tip of the optical fiber creates a first flow disturbance in the moving fluid; and
- at least one flow disturbance element for superimposing a second flow disturbance onto the first flow disturbance.

11. The system of claim 10, wherein the at least one flow disturbance element is stationary with respect to the distal terminating tip of the optical fiber.

12. The system of claim 10, wherein the at least one flow disturbance element is upstream of the distal terminating tip of the optical fiber in a range of 0 cm to 20 cm.

13. The system of claim 12, wherein the at least one flow disturbance element is upstream of the distal terminating tip of the optical fiber in a range of 5 mm to 30 mm.

14. The system of claim 10, wherein the at least one flow disturbance element comprises a protrusion into an inner lumen of an inlet cannula, the protrusion having a width or diameter in a range of 0.2 mm to 1 mm.

15. The system of claim 14, wherein the at least one flow disturbance element has a height sufficient that a flow disturbance reaches the distal terminating tip of the optical fiber.

16. The system of claim 15, wherein the height is in a range of 0.1 mm to 1 mm.

17. The system of claim 10, wherein the at least one flow disturbance element comprises a groove having a depth in a range of 0.5 to 1 mm and an angle to a direction of flow in a range of 15 to 90 degrees.

18. The system of claim 10, wherein the at least one flow disturbance element is a ridge having a height in a range of 0.5 to 1 mm and an angle to a direction of flow in a range of 15 to 90 degrees.

19. The system of claim 9, wherein the light has a wavelength in a range of 390 nm to 750 nm.

20. The system of claim 9, wherein the light is configured to penetrate through blood deeper than 0.6 mm.

21. The system of claim 9, wherein the light has a wavelength in a range of 640 nm to 750 nm.

* * * * *